US008940885B2

(12) United States Patent
Gmeiner

(10) Patent No.: US 8,940,885 B2

(45) **Date of Patent: *Jan. 27, 2015**

(54) CYTOTOXIC NUCLEOTIDES FOR TARGETED THERAPEUTICS

(75) Inventor: William H. Gmeiner, Yadkinville, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 178 days.

This patent is subject to a terminal disclaimer.

(21) Appl. No.: 13/008,614

(22) Filed: Jan. 18, 2011

(65) Prior Publication Data

US 2011/0213135 A1 Sep. 1, 2011

Related U.S. Application Data

(63) Continuation of application No. 11/704,090, filed on Feb. 8, 2007, now abandoned.

(60) Provisional application No. 60/771,323, filed on Feb. 8, 2006.

(51) Int. Cl.

*C07H 21/04* (2006.01)
*C40B 20/04* (2006.01)
*C40B 20/06* (2006.01)

(52) U.S. Cl.

CPC ................ *C40B 20/04* (2013.01); *C40B 20/06* (2013.01)
USPC ........................................................ 536/24.5

(58) Field of Classification Search

USPC ........................................................ 536/24.5
See application file for complete search history.

(56) References Cited

U.S. PATENT DOCUMENTS

| | | | | |
|---|---|---|---|---|
| 5,457,187 | A * | 10/1995 | Gmeiner et al. | 536/25.5 |
| 5,614,505 | A | 3/1997 | Gmeiner et al. | 514/50 |
| 5,660,985 | A | 8/1997 | Pieken et al. | 435/6 |
| 5,663,321 | A * | 9/1997 | Gmeiner et al. | 536/25.5 |
| 5,741,900 | A | 4/1998 | Gmeiner et al. | 536/25.31 |
| 6,342,485 | B1 * | 1/2002 | Gmeiner | 514/44 R |
| 6,613,526 | B2 | 9/2003 | Heilig et al. | 435/6 |
| 6,699,843 | B2 | 3/2004 | Pietras et al. | 514/44 |
| 2004/0249130 | A1 | 12/2004 | Stanton et al. | |
| 2005/0245471 | A1 * | 11/2005 | Balloul et al. | 514/44 |
| 2005/0256071 | A1 | 11/2005 | Davis | |
| 2005/0282190 | A1 | 12/2005 | Shi et al. | |
| 2005/0287128 | A1 | 12/2005 | Guerciolini et al. | |
| 2006/0088864 | A1 | 4/2006 | Smolke et al. | |
| 2006/0246123 | A1 | 11/2006 | Gilboa et al. | |
| 2007/0009476 | A1 | 1/2007 | Wilson et al. | |
| 2010/0261781 | A1 * | 10/2010 | Gmeiner | 514/44 R |

FOREIGN PATENT DOCUMENTS

| | | | |
|---|---|---|---|
| WO | WO 02/33116 | * | 4/2002 |
| WO | WO 2009/046104 A1 | | 4/2009 |

OTHER PUBLICATIONS

Loke et al., PNAS, 86:3474-3478, 1989.*

Corrias et al., *Interaction of human plasma membrane proteins and oligodeoxynucleotides*. Biochem. Pharmacol. 55, 1998, pp. 1221-1227.

Fracasso et al., *Anti-tumor effects of toxins targeted to the prostate specific membrane antigen*, Prostate 53, 2002, pp. 9-23.

Gmeiner et al., *Enhanced DNA-Directed Effects of FdUMP[10] Compared to 5FU*, Nucleosides, Nucleotides & Nucleic Acids, vol. 23, Nos. 1 & 2, 2004, pp. 401-410.

Gmeiner, W.H., *Novel Chemical Strategies for Thymidylate Synthase Inhibition*, Current Medicinal Chemistry, 2005, 12, pp. 191-202.

Liu et al., *Constitutive and Antibody-Induced Internalization of Prostate-specific Membrane Antigen*, Cancer Research 58, Sep. 15, 1981, pp. 4055-4060.

Longley et al., *5-Fluorouracil: Mechanisms of Action and Clinical Strategies*, 2003 Nature Publishing Group, May 2003, vol. 3, pp. 330-338.

Lupold et al., *Identification and Characterization of Nuclease-stabilized RNA Molecules that Bind Human Protstate Cancer Cells via the Prostate-specific Membrane Antigen*, Cancer Research 62, Jul. 15, 2002, pp. 4029-4033.

Morris et al., *High affinity ligands from in vitro selection: complex targets*, Proc Natl. Acad. Sci. USA, vol. 95, Mar. 1998, pp. 2902-2907.

Schulke et al., *The homodimer of prostate-specific membrane antigen is a functional target for cancer therapy*, PNAS, Oct. 28, 2003, vol. 100, No. 22, pp. 12590-12595.

Zuker, Michael, *Mfold web server for nucleic acid folding and hybridization predication*, Nucleic Acids Research, vol. 31, No. 13, Oxford University Press 2003, pp. 3406-3415.

Farokhzad OC et al. Nanoparticle-aptamer bioconjugates: a new approach for targeting prostate cancer cells. Cancer Research. Nov. 1, 2004; 64: 7668-7672.

Dollins CM et al. Assembling OX40 aptamers on a molecular scaffold to create a receptor-activating aptamer. Chemistry & Biology. 2008: 8 pp.

Wullner U et al. Cell-specific induction of apoptosis by rationally designed bivalent aptamer-siRNA transcripts silencing eukaryotic elongation factor 2. Current Cancer Drug Targets. 2008; 8(7): 554-565.

Santulli-Marotto S et al. Multivalent RNA aptamers that inhibit CTLA-4 and enhance tumor immunity. Cancer Research. Nov. 1, 2003; 63: 7483-7489.

Liu J et al. Targeted drug delivery to chemoresistant cells: folic acid derivatization of fdUMP[10] enhances cytotoxicity toward 5-FU-resistant human colorectal tumor cells. J Org Chem. 2001; 66(17): 5655-5663.

Liu C et al. Efficacy and safety of FdUMP[10] in treatment of HT-29 human colon cancer xenografts. International Journal of Oncology. 2002; 21: 303-308.

* cited by examiner

*Primary Examiner* — Brian Whiteman

(74) *Attorney, Agent, or Firm* — Myers Bigel Sibley & Sajovec, P.A.

(57) ABSTRACT

The present invention provides a method of generating a nucleic acid, which specifically binds to an extracellular surface protein expressed by a cell of interest, and which nucleic acid comprises a compound of interest to be delivered to the cell of interest.

7 Claims, 8 Drawing Sheets

FdUMP[5]

5FU

FdU

FdUMP

A

B

SEQUENCE LISTING

```
<160> NUMBER OF SEQ ID NOS: 3

<210> SEQ ID NO 1
<211> LENGTH: 56
<212> TYPE: RNA
<213> ORGANISM: Artificial
<220> FEATURE:
<223> OTHER INFORMATION: Synthetic aptamer

<400> SEQUENCE: 1

gggaggacga ugcggaucag ccauguuuac gucacuccuu gucaauccuc aucggc        56


<210> SEQ ID NO 2
<211> LENGTH: 56
<212> TYPE: RNA
<213> ORGANISM: Artificial
```

-continued

```
<220> FEATURE:
<223> OTHER INFORMATION: Synthetic aptamer

<400> SEQUENCE: 2

caggcaugcc uagcuaagca gcccauggcu uaugcgcgga auauuggcuu ccguuc         56


<210> SEQ ID NO 3
<211> LENGTH: 66
<212> TYPE: RNA
<213> ORGANISM: Artificial
<220> FEATURE:
<223> OTHER INFORMATION: Synthetic aptamer
<220> FEATURE:
<221> NAME/KEY: misc_feature
<222> LOCATION: (42)..(42)
<223> OTHER INFORMATION: n is 5-Fluoro-dU
<220> FEATURE:
<221> NAME/KEY: misc_feature
<222> LOCATION: (46)..(46)
<223> OTHER INFORMATION: n is 5-Fluoro-dU
<220> FEATURE:
<221> NAME/KEY: misc_feature
<222> LOCATION: (49)..(49)
<223> OTHER INFORMATION: n is 5-Fluoro-dU
<220> FEATURE:
<221> NAME/KEY: misc_feature
<222> LOCATION: (52)..(52)
<223> OTHER INFORMATION: n is 5-Fluoro-dU
<220> FEATURE:
<221> NAME/KEY: misc_feature
<222> LOCATION: (57)..(66)
<223> OTHER INFORMATION: n is 5-Fluoro-dU

<400> SEQUENCE: 3

gggaggacga ugcggaucag ccauguuuac gucacuccuu gncaanccnc ancggcnnnn     60

nnnnnn                                                                66
```

CYTOTOXIC NUCLEOTIDES FOR TARGETED THERAPEUTICS

RELATED APPLICATIONS

This application is a continuation of U.S. patent application Ser. No. 11/704,090, filed Feb. 8, 2007 now abandoned, and claims the benefit under 35 U.S.C. §119(e) of U.S. Provisional Patent Application Ser. No. 60/771,323, filed Feb. 8, 2006, the disclosure of each of which is incorporated herein by reference in its entirety.

GOVERNMENT SUPPORT

This invention was made with government support under grants from the Department of Defense and the National Institutes of Health. The government has certain rights to this invention.

FIELD OF INVENTION

The present invention concerns chemotherapeutic molecules and compositions thereof, and methods of use thereof for the treatment of cancer.

BACKGROUND OF THE INVENTION

Cancer is the second-leading cause of death in the United States and is a serious public health concern. The current generation of cytotoxic chemotherapeutic agents used for the treatment of cancer is not curative for a majority of patients. For many cancer patients, the use of chemotherapy extends patient-life by only a few months and often results in serious side effects that reduce the quality of life.

Anticancer drugs that are utilized for cancer chemotherapy include cytotoxic nucleoside analogs (Pratt et al., "Antimetabolites" in The Anticancer Drugs, $2^{nd}$ ed. Oxford University Press, New York. pp. 69-107 (1994)), such as analogs of the four nucleotides that are the principal components of DNA. Examples of cytotoxic analogs include the fluoropyrimidines (FPs) such as 5FU, which are analogs of dU, the precursor for dT, the arabinosyl nucleotides AraC and AraA, which are analogs of dC and dA, respectively, dFdC (gemcitabine), which is an analog of dC, and 6-mercaptopurine, which is an analog of dI, the precursor of dG.

The current paradigm in chemical drug development involves restrictions on the molecular weight and the charge of candidate drugs. The rationale for these restrictions is that drugs must have high bioavailability and must enter cells either by passive diffusion or by well-characterized molecular transport processes. Thus, while the activated forms of nucleoside analogs are typically 5'-O-mono-, di-, or tri-phosphates, cytotoxic nucleoside analogs are either administered as the nucleobase, if the active form of the drug is the 2'-deoxyribonucleotide (e.g. 5FU as a precursor for FdUMP), or as the nucleoside, if the activated form of the drug has a non-native sugar (e.g. AraC as a precursor for AraCTP). However, 2'-deoxyribonucleosides are generally ineffective as drugs because of the facile cleavage of the glycosidic bond.

The requirement for intracellular metabolic activation of these drugs decreases their effectiveness for at least two reasons: 1) cancer cells can become resistant to the drug by down-regulating the expression of cellular enzymes that are required for metabolic activation; and 2) competing metabolic processes may divert the drug to undesirable products in the cell. For example, 5FU is administered as a precursor to FdUMP but is also metabolized to FUTP and incorporated into RNA, resulting in toxicity towards cells of the gasterointestinal tract (Pritchard et al., Proc. Natl. Acad. Sci. USA 94: 1795-1799 (1997)).

The principal cause for the ineffectiveness of cytotoxic chemotherapeutic drugs in current use (e.g., 5-fluorouracil (5FU)) is a failure of the activated form of the drug to accumulate in cancer cells at sufficient concentrations to cause cancer cell death (Longley et al., Nature Cancer 3: 330-338 (2003)). Malignant cells that survive drug treatment become drug-resistant, and refractory to further chemotherapy.

For example, despite great efforts utilizing conventional chemotherapy strategies, metastatic prostate cancer (PC) currently remains incurable and an inevitably fatal disease. This is largely due to the fact that chemotherapeutic drugs are not effective at killing tumors in late-stage PC because PC cells do not accumulate drugs at sufficient concentrations to cause cell death. The ability to deliver activated cytotoxic drugs specifically to PC cells in vivo is likely to result in a reduction of the mortality rate (currently 30,000 per year) for patients with advanced PC (American Cancer Society Facts and Figures 2004.

Targeted delivery of cytotoxic drugs is expected to decrease the morbidity associated with cancer chemotherapy. Thus, there is a great need for innovative approaches to improve the long-term survival of patients suffering with this disease.

SUMMARY OF THE INVENTION

Provided herein are methods of generating a nucleic acid of interest, which nucleic acid specifically binds to an extracellular surface protein expressed by a cell of interest, and which nucleic acid is capable of being internalized by said cell of interest, said method comprising the steps of: (a) combining a first pool comprising different nucleic acids with said extracellular surface protein; (b) selecting a first subpopulation of nucleic acids from said first pool, said first subpopulation comprising at least one nucleic acid that specifically binds to said extracellular surface protein; (c) amplifying said at least one nucleic acid of said first subpopulation; and (d) selecting a second subpopulation comprising at least one nucleic acid species from said first subpopulation which is internalized by said cell of interest. Cells of interest may be, e.g., cancer cells, microbial cells, parasitic cells, etc. The nucleic acid may comprise a compound of interest, such as an active compound (e.g., cytotoxic nucleotides) and/or a detectable group.

Also provided are methods of generating a nucleic acid of interest, which nucleic acid specifically binds to an extracellular surface protein expressed by a cell of interest, which nucleic acid is capable of being internalized by said cell of interest, and which nucleic acid comprises one or more compounds of interest to be delivered to said cell of interest, said method comprising the steps of: (a) combining a first pool comprising different nucleic acids with said extracellular surface protein; (b) selecting a first subpopulation of nucleic acids from said first pool, said first subpopulation comprising at least one nucleic acid that specifically binds to said extracellular surface protein; (c) amplifying said at least one nucleic acid of said first subpopulation; (d) selecting a second subpopulation comprising at least one nucleic acid species from said first subpopulation which is internalized by said cell of interest; (e) determining a first chemical structure of a nucleic acid from said second population; (f) determining a second chemical structure of a nucleic acid which is an analog of said nucleic acid from said second population, said analog comprising one or more of said compounds of interest; (g) analyzing the folding properties of said first chemical structure; (h) analyzing the folding properties of said second chemical structure; (i) comparing the folding properties of said first chemical structure with that of said second chemical structure; and (j) generating a nucleic acid of interest based upon said comparing.

BRIEF DESCRIPTION OF THE DRAWINGS

FIGS. 5E and 5F, respectively, show the phase contrast and fluorescence microscopy images of PC3 cells following 30 min exposure to the modified aptamer.

DETAILED DESCRIPTION OF THE PREFERRED EMBODIMENTS

Figure 1:
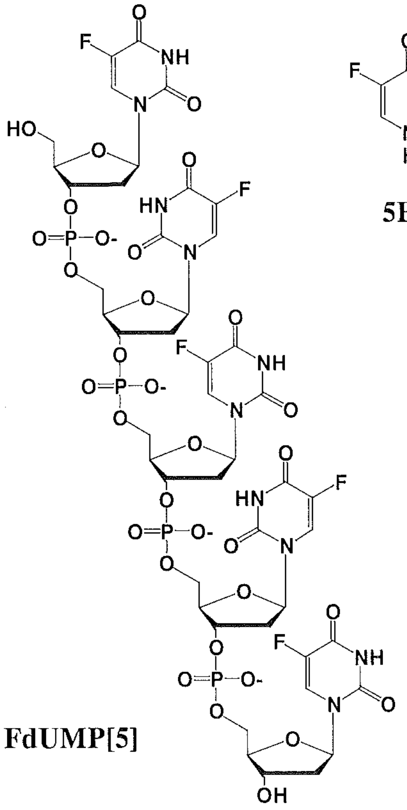
FIG. 1. Structure of FdUMP[5], the linear homopolymer of FdUMP nucleotides of length 5, and the chemical structures for 5-fluorouracil (5FU), 5-fluoro-2'-deoxyuridine (FdU), and 5-fluoro-2'-deoxyuridine-5'-O-monophosphate (FdUMP).
Figure 1:
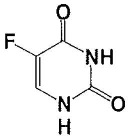
Figure 1:
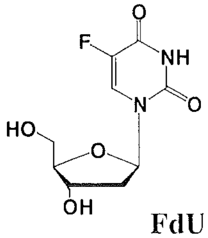
Figure 1:
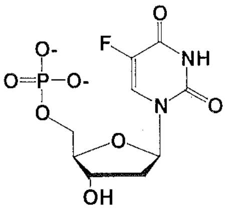

The present invention is explained in greater detail below. This description is not intended to be a detailed catalog of all the different ways in which the invention may be implemented, or all of the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

As used in the description of the invention and the appended claims, the singular forms "a", "an" and "the" are intended to include the plural forms as well, unless the context clearly indicates otherwise. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" refers to and encompasses any and all possible combinations of one or more of the associated listed items, as well as the lack of combinations when interpreted in the alternative ("or").

The disclosures of all Patent references cited herein are incorporated herein by reference in their entirety.

"Compound of interest" as used herein includes, but is not limited to, detectable compounds and active compounds.

"Detectable compounds" as used herein include, but are not limited to, radiolabels (e.g., $^{35}S$, $^{125}I$, $^{32}P$, $^{3}H$, $^{14}C$, $^{131}I$), enzyme labels (e.g., horseradish peroxidase, alkaline phosphatase), gold beads, chemiluminescence labels, ligands (e.g., biotin, digoxin) and/or fluorescence labels (e.g., rhodamine, phycoerythrin, fluorescein), a fluorescent protein including, but not limited to, green fluorescent protein or one of its many modified forms, a nucleic acid segment in accordance with known techniques, and energy absorbing and energy emitting agents.

"Active compound" as used herein includes, but is not limited to, cytotoxic nucleosides or nucleotides, antisense oligonucleotides, radionuclides, energy absorbing and energy emitting agents, and other cytotoxic agents. Other cytotoxic agents include, but are not limited to, ricin (or more particularly the ricin A chain), aclacinomycin, diphtheria toxin, Monensin, Verrucarin A, Abrin, Tricothecenes, and Pseudomonas exotoxin A, taxol, cytochalasin B, gramicidin D, ethidium bromide, emetine, mitomycin, etoposide, tenoposide, anti-mitotic agents such as the vinca alkaloids (e.g., vincristine and vinblastine), colchicin, anthracyclines such as doxorubicin and daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP)), and antibiotics, including but not limited to, dactinomycin (formerly actinomycin), bleomycin, mithramycin, calicheamicin, and anthramycin (AMC).

"Cytotoxic nucleoside or nucleotide" as used herein includes, but is not limited to, 2',2'-difluorodeoxycytidine, (dFdC, gemcitabine), 5-fluorouracil (5-FU), 5-fluoro-2'-deoxyuridine-5'-O-monophosphate (FdUMP), 5-fluoro-2'-deoxyuridine (FdU), arabinosylcytosine (Ara-C), arabinosyl adenosine (Ara-A), fluorouracil arabinoside, mercaptopurine riboside, 5-aza-2'-deoxycytidine, arabinosyl 5-azacytosine, 6-azauridine, azaribine, 6-azacytidine, trifluoro-methyl-2'-deoxyuridine, thymidine, thioguanosine, 3-deazautidine, 2-Chloro-2'-deoxyadenosine (2-CdA), AZT (azidothymidine), 2',3'-dideoxyinosine (ddI), cytotoxic nucleoside-corticosteroid phosphodiester, 5-bromodeoxyuridine 5'-methylphosphonate, 5-fluorodeoxyuridine (FdUrd), fludarabine (2-F-ara-AMP), 6-mercaptopurine and 6-thioguanine, 2-chlorodeoxyadenosine (CdA), 2'-deoxycoformycin (pentostatin), 4'-thio-beta-D-arabinofuranosylcytosine, and any other cytotoxic dA, dC, dT, dG, dU, or homologs thereof.

In some embodiments, modified oligonucleotides incorporate activated anticancer drugs into three-dimensional nucleic acid structures that selectively bind to and are internalized by cancer cells. Modified oligonucleotides are comprised, in part, of relatively low molecular weight activated drugs. Thus, the three-dimensional structures of modified oligonucleotides that facilitate selective binding to and penetration of targeted cells are formed based upon the chemical and structural properties of the component drugs. In preferred embodiments, the activated drug is 5-fluoro-2'-deoxyuridine-5'-O-monophosphate (FdUMP).

The term "antisense oligonucleotide," as used herein, refers to a nucleic acid that is complementary to and specifically hybridizes to a specified DNA or RNA sequence. Antisense oligonucleotide includes, but is not limited to, ribozymes, small interfering RNAs, short hairpin RNAs, micro RNAs, triplex-forming oligonucleotides, and/or PNAs. Antisense oligonucleotides and nucleic acids that encode the same can be made in accordance with conventional techniques. See, e.g., U.S. Pat. No. 5,023,243 to Tullis; U.S. Pat. No. 5,149,797 to Pederson et al. Those skilled in the art will appreciate that it is not necessary that the antisense oligonucleotide be fully complementary to a target sequence, as long as the degree of sequence similarity is sufficient for the antisense nucleotide sequence to specifically hybridize to its target and reduce production of the polypeptide (e.g., by at least about 30%, 40%, 50%, 60%, 70%, 80%, 90%, or 95% or more).

"Radionuclide" as described herein may be any radionuclide suitable for delivering a therapeutic dosage of radiation to a tumor or cancer cell, including, but not limited to, $^{225}$Ac, $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Re, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Ser, $^{35}$S, $^{177}$Ta, $^{117}$mSn, $^{121}$Sn, $^{166}$Yb, $^{169}$Yb, $^{90}$Y, $^{212}$Bi, $^{213}$Bi, $^{119}$Sb, $^{197}$Hg, $^{97}$Ru, $^{100}$Pd, $^{101m}$Rh, and $^{212}$Pb.

"Energy absorbing and energy emitting agent" as used herein includes, but is not limited to, diagnostic agents, contrast agents, iodinated agents, radiopharmaceuticals, fluorescent compounds and fluorescent compounds coencapsulated with a quencher, agents containing MRS/MRI sensitive nuclides, genetic material encoding contrast agents, and energy absorbing and heat emitting nanomaterials including, but not limited to, single-walled nanotubes and gold nanocages. Some examples of contrast agents include, but are not limited to, metal chelates, polychelates, multinuclear cluster complexes (U.S. Pat. No. 5,804,161), halogenated xanthene or a functional derivative of a halogenated xanthene (U.S. Pat. No. 6,986,740), gadolinium-diethylenetriaminepentaacetic acid (gadopentetate dimeglumine, GdDTPA; Magnavist), gadoteridol (ProHance), gadodiamide, gadoterate meglumine (Gd-DOTA), gadobenate dimeglumine (Gd-BOPTA/Dimeg; MultiHance), mangafodipir trisodium (Mn-DPDP), ferumoxides, paramagnetic analogue of doxorubicin, and ruboxyl (Rb). Some examples of iodinated agents include, but are not limited to, diatrizoate (3,5-di(acetamido)-2,4,6-triiodobenzoic acid), iodipamide (3,3'-adipoyl-diimino-di(2,4,6-triiodobenzoic acid), acetrizoate [3-acetylamino-2,4,6-triiodobenzoic acid], aminotrizoate [3-amino-2,4,6-triiodobenzoic acid]), and iomeprol. Examples of radiopharmaceuticals include, but are not limited to, fluorine-18 fluorodeoxyglucose ([18F]FDG), Tc-99m Depreotide, carbon-11 hydroxyephedrine (HED), [18F] setoperone, [methyl-11C]thymidine, 99mTc-hexamethyl propyleneamine oxime (HMPAO), 99mTc-L, L-ethylcysteinate dimer (ECD), 99mTc-sestamibi, thallium 201, I-131 metaiodobenzylguanidine (MIBG), 123I-N-isopropyl-p-iodoamphetamine (IMP), 99mTc-hexakis-2-methoxyisobutylisonitrile (MIBI), 99mTc-tetrofosmin. Examples of agents containing MRS/MRI sensitive nuclides include, but are not limited to, perfluorocarbons and fluorodeoxyglucose. Examples of genetic material encoding contrast agents include, but are not limited to, paramagnetic reporter genes such as ferredoxin; paramagnetic tag(s) on liposomal lipids such as paramagnetic chelating groups added to PEG; detectable probes; and luciferin/luciferase reporter system.

"Nucleic acid" as used herein refers to single- or double-stranded molecules which may be deoxyribonucleic acid (DNA), ribonucleic acid (RNA), or homologs thereof such as peptide nucleic acid (PNA), which is comprised of stretches of nucleic acid polymers linked together by peptide linkers, or a combination thereof. The nucleic acid may represent a coding strand or its complement. The nucleic acids of this invention may be comprised of any combination of naturally-occurring nucleosides (A, G, C, T, U), and/or the nucleic acids may comprise nucleoside or nucleotide analogs and/or derivatives as are well known in the art, including cytotoxic, synthetic, rare, non-natural bases or altered nucleotide bases. A nucleic acid molecule in the form of a polymer of DNA may be comprised of one or more segments of cDNA, genomic DNA or synthetic DNA. In addition, a modification can be incorporated to reduce exonucleolytic degradation, such as a reverse (3'→5') linkage at the 3'-terminus.

"Cell of interest" as used herein may be any suitable cell, including but not limited to cancer cells, tissue cells generally (e.g., muscle, bone, nerve, liver, lung, etc.), pathological and non-pathological microbial cells (e.g., bacterial, mycobacterial, spirochetal rickettsial, chlamydial, mycoplasmal, and fungal, etc.), parasitic cells (e.g., protozoal, helminth, etc.), and plant cells, etc.

"Cancer cell" as used herein may be any cancer cell, including, but not limited to, lung, colon, ovarian, prostate, bone, nerve, liver, leukemia, and lymphoma cells.

"Bacterial cell" as used herein may be any bacterial cell including, but not limited to, Gram-negative bacteria, Gram-positive bacteria and other bacteria.

Examples of Gram-negative bacteria include, but are not limited to, bacteria of the genera, *Salmonella, Escherichia, Klebsiella, Haemophilus, Pseudomonas, Proteus, Neisseria, Vibro, Helicobacter, Brucella, Bordetella, Legionella, Campylobacter, Francisella, Pasteurella, Yersinia, Bartonella, Bacteroides, Streptobacillus, Spirillum, Moraxella* and *Shigella*. Furthermore, bacterial cell of interest includes Gram-negative bacteria including, but not limited to, *Escherichia coli, Pseudomonas aeruginosa, Neisseria meningitides, Neisseria gonorrhoeae, Salmonella typhimurium, Salmonella entertidis, Klebsiella pneumoniae, Haemophilus influenzae, Haemophilus ducreyi, Proteus mirabilis, Vibro cholera, Helicobacter pylori, Brucella abortis, Brucella melitensis, Brucella suis, Bordetella pertussis, Bordetella parapertussis, Legionella pneumophila, Campylobacter fetus, Campylobacter jejuni, Francisella tularensis, Pasteurella multocida, Yersinia pestis, Bartonella bacilliformis, Bacteroides fragilis, Bartonella henselae, Streptobacillus moniliformis, Spirillum minus, Moraxella catarrhalis* (*Branhamella catarrhalis*), and *Shigella dysenteriae*.

Examples of Gram-positive bacteria include, but are not limited to, bacteria of the genera *Listeria, Staphylococcus, Streptococcus, Bacillus, Corynebacterium, Peptostreptococcus*, and *Clostridium*. Furthermore, bacterial cell of interest includes Gram-positive bacteria including, but not limited to, *Listeria monocytogenes, Staphylococcus aureus, Streptococcus pyogenes, Streptococcus pneumoniae, Bacillus cereus, Bacillus anthracia, Clostridium botulinum, Clostridium per-*

*fringens, Clostridium difficile, Clostridium tetani, Corynebacterium diphtheriae, Corynebacterium ulcerans*, and *Peptostreptococcus anaerobius.*

Additional bacteria include bacterial genera including, but not limited to, *Actinomyces, Propionibacterium, Nocardia* and *Streptomyces*. Furthermore, bacterial cell of interest of the present invention includes, but is not limited to, *Actinomyces israeli, Actinomyces gerencseriae, Actinomyces viscosus, Actinomyces naeslundii, Propionibacterium propionicus, Nocardia asteroides, Nocardia brasiliensis, Nocardia otitidiscaviarum* and *Streptomyces somaliensis.*

"Mycobacterial cell" as used herein may be any mycobacterial cell, including but not limited to mycobacteria belonging to the mycobacteria families including, but not limited to, Mycobacteriaceae. Additionally, mycobacterial cell of the present invention includes, but is not limited to, *Mycobacterium tuberculosis, Mycobacterium leprae, Mycobacterium avium-intracellulare, Mycobacterium kansasii*, and *Mycobacterium ulcerans.*

"Spirochetal cell" as used herein may be any spirochetal cell, including but not limited to spirochetes belonging to the genera including, but not limited to, *Treponema, Leptospira*, and *Borrelia*. Additionally, spirochetal cell of the present invention includes, but is not limited to, *Treponema palladium, Treponema pertenue, Treponema carateum, Leptospira interrogans, Borrelia burgdorferi*, and *Borrelia recurrentis.*

"Rickettsial cell" as used herein may be any rickettsial cell, including but not limited to rickettsia belonging to the genera including, but not limited to, *Rickettsia, Ehrlichia, Orienta, Bartonella* and *Coxiella*. Furthermore, rickettsial cell includes, but is not limited to, *Rickettsia rickettsii, Rickettsia akari, Rickettsia prowazekii, Rickettsia typhi, Rickettsia conorii, Rickettsia sibirica, Rickettsia australis, Rickettsia japonica, Ehrlichia chaffeensis, Orienta tsutsugamushi, Bartonella quintana*, and *Coxiella burni.*

"Chlamydial cell" as used herein may be any chlamydial cell belonging to the genera including, but not limited to, *Chlamydia*. Furthermore, chlamydial cell of the present invention includes, but is not limited to, *Chlamydia trachomatis, Chlamydia caviae, Chlamydia pneumoniae, Chlamydia muridarum, Chlamydia psittaci*, and *Chlamydia pecorum.*

"Mycoplasmal cell" as used herein may be any mycoplasmal cell belonging to the genera including, but not limited to, *Mycoplasma* and *Ureaplasma*. In addition, mycoplasmal cell includes but is not limited to, *Mycoplasma pneumoniae, Mycoplasma hominis, Mycoplasma genitalium*, and *Ureaplasma urealyticum.*

"Fungal cell" as used herein may be any fungal cell belonging to the genera including, but not limited to, *Aspergillus, Candida, Cryptococcus, Coccidioides, Tinea, Sporothrix, Blastomyces, Histoplasma, Pneumocystis* and *Saccharomyces*. Additionally, fungal cell of the present invention includes, but is not limited to, *Aspergillus fumigatus, Aspergillus flavus, Aspergillus niger, Aspergillus terreus, Aspergillus nidulans, Candida albicans, Coccidioides immitis, Cryptococcus neoformans, Tinea unguium, Tinea corporis, Tinea cruris, Sporothrix schenckii, Blastomyces dermatitidis, Histoplasma capsulatum, Histoplasma duboisii*, and *Saccharomyces cerevisiae.*

Compounds of the present invention may also be used to control microbes in industrial fermentation. "Parasitic cell" as used herein may include any parasitic cell belonging to the genera including, but not limited to, *Entamoeba, Dientamoeba, Giardia, Balantidium, Trichomonas, Cryptosporidium, Isospora, Plasmodium, Leishmania, Trypanosoma, Babesia, Naegleria, Acanthamoeba, Balamuthia, Enterobius, Strongyloides, Ascaradia, Trichuris, Necator, Ancylostoma, Uncinaria, Onchocerca, Mesocestoides, Echinococcus, Taenia, Diphylobothrium, Hymenolepsis, Moniezia, Dicytocaulus, Dirofilaria, Wuchereria, Brugia, Toxocara, Rhabditida, Spirurida, Dicrocoelium, Clonorchis, Echinostoma, Fasciola, Fascioloides, Opisthorchis, Paragonimus*, and *Schistosoma*. Additionally, parasitic cell of the present invention includes, but is not limited to, *Entamoeba histolytica, Dientamoeba fragilis, Giardia lamblia, Balantidium coli, Trichomonas vaginalis, Cryptosporidium parvum, Isospora belli, Plasmodium malariae, Plasmodium ovale, Plasmodium falciparum, Plasmodium vivax, Leishmania braziliensis, Leishmania donovani, Leishmania tropica, Trypanosoma cruzi, Trypanosoma brucei, Babesia divergens, Babesia microti, Naegleria fowleri, Acanthamoeba culbertsoni, Acanthamoeba polyphaga, Acanthamoeba castellanii, Acanthamoeba astronyxis, Acanthamoeba hatchetti, Acanthamoeba rhysodes, Balamuthia mandrillaris, Enterobius vermicularis, Strongyloides stercoralis, Strongyloides fulleborni, Ascaris lumbricoides, Trichuris trichiura, Necator americanus, Ancylostoma duodenale, Ancylostoma ceylanicum, Ancylostoma braziliense, Ancylostoma caninum, Uncinaria stenocephala, Onchocerca volvulus, Mesocestoides variabilis, Echinococcus granulosus, Taenia solium, Diphylobothrium latum, Hymenolepis nana, Hymenolepis diminuta, Moniezia expansa, Moniezia benedeni, Dicytocaulus viviparous, Dicytocaulus filarial, Dicytocaulus arnfieldi, Dirofilaria repens, Dirofilaria immitis, Wuchereria bancrofti, Brugia malayi, Toxocara canis, Toxocara cati, Dicrocoelium dendriticum, Clonorchis sinensis, Echinostoma, Echinostoma ilocanum, Echinostoma jassyenese, Echinostoma malayanum, Echinostoma caproni, Fasciola hepatica, Fasciola gigantica, Fascioloides magna, Opisthorchis viverrini, Opisthorchis felineus, Opisthorchis sinensis, Paragonimus westermani, Schistosoma japonicum, Schistosoma mansoni, Schistosoma haematobium* and *Schistosoma haematobium.*

"Extracellular surface protein" as used herein may be any extracellular surface protein including, but not limited to, growth factor receptors, receptor tyrosine kinases, folate hydrolases, GPI-anchored cell surface antigens, pumps, and cell surface receptors including, but not limited to, G-protein coupled receptors, ion channel-linked receptors, and enzyme-linked receptors.

Extracellular surface proteins of interest may be those "differentially expressed" by a targeted cell of interest, in comparison to a cell that is not to be targeted by a cytotoxic nucleotide. For example, the cancer cells differ from normal cells in many respects, including the up- or down-regulation of numerous genes. Among the genes that are differentially regulated in cancer cells are genes that encode proteins that are expressed on the extracellular surface. As an example, specific proteins are expressed on the extracellular surface of prostate cancer (PC) cells that are not expressed (or are expressed at very low levels) by normal prostatic epithelial cells and cells from other normal tissues. Extracellular proteins that are expressed exclusively by PC cells are excellent candidates for specific targeting of malignant cells with anticancer drugs. Cytotoxic oligodeoxynucleotides (ODNs) may be internalized by malignant cells that express specific ODN receptor proteins (Corrias et al., Biochem. Pharmacol. 55: 1221-1227 (1998)). The expression of prostate specific membrane antigen (PSMA) is limited to PC cells and cells of the tumor neovasculature (Schulke et al., Proc. Natl. Acad. Sci. USA 100: 12590-12595 (2003)). A second protein that displays characteristics suitable for developing targeted therapeutics for PC is prostate stem cell antigen (PSCA; Saffran et al., Proc. Natl. Acad. Sci. USA 98: 2658-2663 (2001)).

Compounds of the present invention may also be used for the treatment of a viral disease in a cell of interest. Viral diseases include, but are not limited to, those caused by viruses belonging to the viral families including, but not limited to, Flaviviridae, Arenaviradae, Bunyaviridae, Filoviridae, Poxviridae, Togaviridae, Paramyxoviridae, Herpesviridae, Picornaviridae, Caliciviridae, Reoviridae, Rhabdoviridae, Papovaviridae, Parvoviridae, Adenoviridae, Hepadnaviridae, Coronaviridae, Retroviridae, and Orthomyxoviridae. Furthermore, viral diseases that can be treated using the compounds of the present invention can be caused by the viruses including, but not limited to, Yellow fever virus, St. Louis encephalitis virus, Dengue virus, Hepatitis G virus, Hepatitis C virus, Bovine diarrhea virus, West Nile virus, Japanese B encephalitis virus, Murray Valley encephalitis virus, Central European tick-borne encephalitis virus, Far eastern tick-born encephalitis virus, Kyasanur forest virus, Louping ill virus, Powassan virus, Omsk hemorrhagic fever virus, Kumilinge virus, Absetarov anzalova hypr virus, Ilheus virus, Rocio encephalitis virus, Langat virus, Lymphocytic choriomeningitis virus, Junin virus, Bolivian hemorrhagic fever virus, Lassa fever virus, California encephalitis virus, Hantaan virus, Nairobi sheep disease virus, Bunyamwera virus, Sandfly fever virus, Rift valley fever virus, Crimean-Congo hemorrhagic fever virus, Marburg virus, Ebola virus, Variola virus, Monkeypox virus, Vaccinia virus, Cowpox virus, Orf virus, Pseudocowpox virus, Molluscum contagiosum virus, Yaba monkey tumor virus, Tanapox virus, Raccoonpox virus, Camelpox virus, Mousepox virus, Tanterapox virus, Volepox virus, Buffalopox virus, Rabbitpox virus, Uasin gishu disease virus, Sealpox virus, Bovine papular stomatitis virus, Camel contagious ecthyma virus, Chamios contagious ecthyma virus, Red squirrel parapox virus, Juncopox virus, Pigeonpox virus, Psittacinepox virus, Quailpox virus, Sparrowpox virus, Starlingpox virus, Peacockpox virus, Penguinpox virus, Mynahpox virus, Sheeppox virus, Goatpox virus, Lumpy skin disease virus, Myxoma virus, Hare fibroma virus, Fibroma virus, Squirrel fibroma virus, Malignant rabbit fibroma virus, Swinepox virus, Yaba-like disease virus, Albatrosspox virus, Cotia virus, Embu virus, Marmosetpox virus, Marsupialpox virus, Mule deer poxvirus virus, Volepox virus, Skunkpox virus, Rubella virus, Eastern equine encephalitis virus, Western equine encephalitis virus, Venezuelan equine encephalitis virus, Sindbis virus, Semliki forest virus, Chikungunya virus, O'nyong-nyong virus, Ross river virus, Parainfluenza virus, Mumps virus, Measles virus (rubeola virus), Respiratory syncytial virus, Herpes simplex virus type 1, Herpes simplex virus type 2, Varicella-zoster virus, Epstein-Barr virus, Cytomegalovirus, Human b-lymphotrophic virus, Human herpesvirus 7, Human herpesvirus 8, Poliovirus, Coxsackie A virus, Coxsackie B virus, ECHOvirus, Rhinovirus, Hepatitis A virus, Mengovirus, ME virus, Encephalomyocarditis (EMC) virus, MM virus, Columbia SK virus, Norwalk agent, Hepatitis E virus, Colorado tick fever virus, Rotavirus, Vesicular stomatitis virus, Rabies virus, Papilloma virus, BK virus, JC virus, B19 virus, Adeno-associated virus, Adenovirus, serotypes 3, 7, 14, 21, Adenovirus, serotypes 11, 21, Adenovirus, Hepatitis B virus, Coronavirus, Human T-cell lymphotrophic virus, Human immunodeficiency virus, Human foamy virus, Influenza viruses, types A, B, C, and Thogotovirus.

Additionally, compounds of the present invention may be used as an herbicide. The compounds of the present invention may be applied to the surface of the plant including, but not limited to, leaves, stems, flowers, fruits, roots, cells or callus tissue. Alternatively, the compounds of the present invention may be introduced into the plant via methods standard in the art including, but not limited to, microinjection, electroporation, particle bombardment, and *Agrobacterium*-mediated transformation.

Further, compounds of the present invention may also be used for treatment of infection of plants and plant cells by plant pathogens, the plant pathogens including, but not limited to, bacteria, fungi, oomycetes, viruses, and nematodes. For the purpose of treatment of plant pathogenic infections, the compounds of the present invention may be applied to the surface of a plant including, but not limited to, leaves, stems, flowers, fruits, roots, cells or callus tissue. Alternatively, the compounds of the present invention may be introduced into the plant via methods standard in the art including, but not limited to, microinjection, electroporation, particle bombardment, and *Agrobacterium*-mediated transformation.

As used herein, the term "treat" or "treatment" refers to an action resulting in a reduction in the severity of the subject's condition, wherein the condition is at least partially improved or ameliorated, and/or there is some alleviation, mitigation or decrease in at least one clinical symptom (or agricultural index for plants), and/or there is a delay in the progression of the condition, and/or prevention or delay of the onset of the condition. Thus, the term "treat" refers to both prophylactic and therapeutic treatment regimes. Compounds generated by the methods of the present invention may be used for the diagnosis and/or treatment of human subjects, or animal subjects for veterinary or drug development purposes. Examples of animal subjects include mammalian (e.g., dog, cat, mouse, rat, horse, cow, pig, sheep, etc.), reptile, amphibian, and avian (e.g., parrot, budgie, chicken, turkey, duck, geese, quail, pheasant) subjects.

A first pool of nucleic acids used to carry out the present invention may be comprised of range of about $10^6$, $10^8$, $10^{10}$, $10^{11}$, $10^{12}$, or $10^{13}$, to a range of about $10^{14}$, $10^{15}$, $10^{16}$, $10^{18}$, $10^{20}$, $10^{21}$, $10^{22}$, or $10^{23}$ nucleic acid species. In some embodiments, the first pool of nucleic acids comprises about $10^{10}$ to $10^{18}$ nucleic acid species. In further embodiments, the first pool of nucleic acids comprises about $10^{13}$ to $10^{14}$ nucleic acid species. In still further embodiments, the first pool of nucleic acids comprises $10^{15}$ nucleic acid species.

Figure 2:
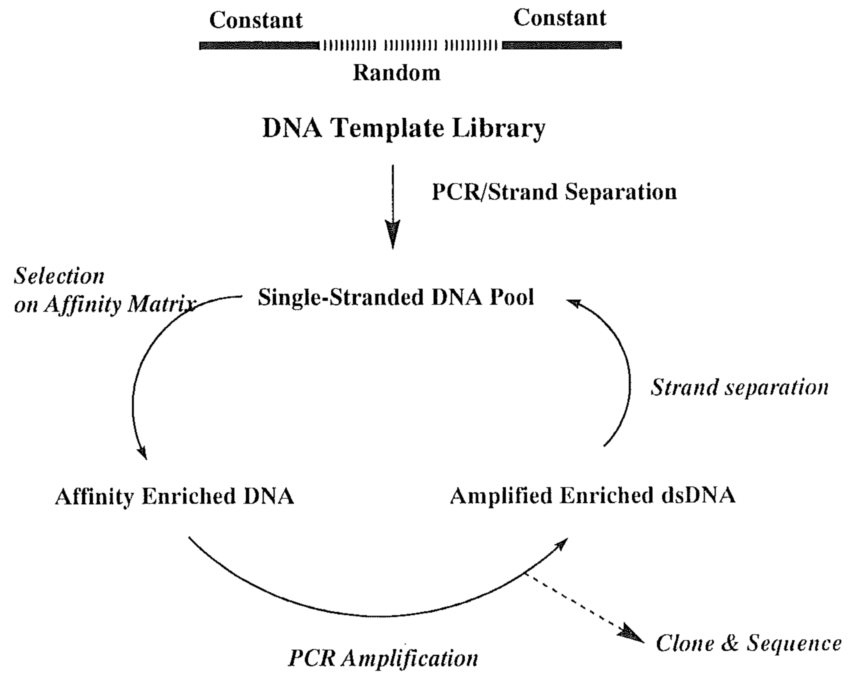
FIG. 2. Diagram of a selection of a first pool of nucleotides that selectively bind to a differentially expressed extracellular surface protein bound to an affinity matrix. The pool comprises nucleotides having two constant regions flanking a random sequence region.

The size of the nucleic acids species within the first pool can be in a range of about 30 nucleotides to about 150 nucleotides. In preferred embodiments, the nucleic acid species of the present invention comprises three regions: a "random" region flanked by two "constant" regions, as illustrated in FIG. 2. The two "constant" regions need not be identical to each other, but comprise known nucleotide sequences. These "constant" regions are used for the annealing of PCR primers during PCR amplification. The lengths of the "constant" regions of the present invention can be in a range of about 8 nucleotides to about 35 nucleotides. In some embodiments the lengths of the "constant" regions are in a range of about 12 nucleotides to about 22 nucleotides. The length of one "constant" region need not be the same as the length of the other "constant" region, and indeed each region may be modified in length and/or sequence based on folding predictions or results following the identification of optimal "random" regions.

The "random" region of the nucleic acids species within the first pool consists of random arrangements of nucleotide sequences. Those "random" regions that selectively bind to a target of interest are selected for during the selection of a first subpopulation of interest, and become the second pool of nucleic acid species. However, in some embodiments there is some predetermined bias contained within the "random" regions. The predetermined bias may be performed to facilitate the inclusion of particular cytotoxic nucleotides. For instance, the first pool of nucleic acids may include a greater representation of a particular nucleoside (A, C, G, T, U). In another embodiment, the nucleic acid pool may include a lesser representation of a particular nucleoside (A, C, G, T, U). In a further embodiment, the nucleic acid pool may include a specific sequence element that may confer antisense or antigene properties to all of the members of the resulting subpopulation.

In some embodiments, the lengths of the nucleic acids species within the first pool includes the "constant" regions, wherein the size of the nucleic acids species can be in a range of about 45 nucleotides to about 130 nucleotides in length. In other embodiments, the size of the nucleic acids species within the first pool can be in a range from about 60 nucleotides to about 100 nucleotides in length. In further embodiments, the size of the nucleic acids species within the first pool can be in a range from about 65 nucleotides to about 80 nucleotides in length. An additional embodiment of the present invention comprises a first pool of nucleic acid species, wherein the size of the nucleic acid species is about 70 nucleotides in length.

In some embodiments, the lengths of the nucleic acids species within the first pool does not include the "constant" regions, wherein the size of the nucleic acids species can be in a range of about 20 nucleotides to about 105 nucleotides in length. In other embodiments of the present invention, the size of the nucleic acids species within the first pool can be in a range from about 35 nucleotides to about 75 nucleotides in length. In further embodiments, the size of the nucleic acids species within the first pool can be in a range from about 40 nucleotides to about 55 nucleotides in length. An additional embodiment of the present invention comprises a first pool of nucleic acid species, wherein the size of the nucleic acids species is about 45 nucleotides in length. A still further embodiment of the present invention comprises a first pool of nucleic acid species, wherein the size of the nucleic acid species is about 30 nucleotides in length.

In some embodiments of the present invention, the first pool of nucleic acid species comprises about $10^{13}$ to $10^{14}$ nucleic acid species, wherein the nucleic acid species are about 70 nucleotides in length including the "constant" regions. In further embodiments, the first pool of nucleic acid species comprises about $10^{15}$ nucleic acid species, wherein the nucleic acid species are about 70 nucleotides in length including the "constant" regions.

In some embodiments of the present invention, the first pool of nucleic acid species comprises about $10^{13}$ to $10^{14}$ nucleic acid species, wherein the nucleic acid species are about 30 nucleotides in length not including the "constant" regions. In a further embodiment, the first pool of nucleic acid species comprises about $10^{15}$ nucleic acid species, wherein the nucleic acid species are about 30 nucleotides in length not including the "constant" regions.

The step of combining the first pool of nucleic acids with the extracellular surface protein may be random or it may be performed with some predetermined bias. The predetermined bias may be performed to facilitate the inclusion of particular cytotoxic nucleotides. In one embodiment, the first pool of nucleic acids may include a greater representation of a particular nucleoside (A, C, G, T, U). In another embodiment, the nucleic acid pool may include a lesser representation of a particular nucleoside (A, C, G, T, U). In a further embodiment, the nucleic acid pool may include a specific sequence element that may confer antisense or antigene properties to all of the members of the resulting subpopulation. This predetermined bias may be found in any portion of the nucleic acids, including the random region and/or either or both of the constant regions (See FIG. 2).

The step of selecting a first subpopulation of nucleic acids from the first pool, wherein the first subpopulation comprises at least one nucleic acid that binds specifically to the extracellular surface protein of interest, may be done using any method standard in the art, including, but not limited to, such methods as affinity chromatography, capillary eletrophoresis, field flow fractionation chromatography and surface plasmon resonance. The methods of capillary electrophoresis and field flow fractionation chromatography may be further combined with mass spectrometry to obtain sequence information on the selected first subpopulation of nucleic acids. The step of selecting may be performed once, or the nucleic acids from the first pool may be subjected to additional rounds of selection to identify those nucleic acids with high affinity for the extracellular surface protein of interest.

"Amplification" or "amplify" as used herein means the construction of multiple copies of a nucleic acid sequence, or multiple copies complementary to the nucleic acid sequence, using at least one of the nucleic acid sequences as a template. The step of amplifying nucleic acids may be any method standard in the art for amplifying nucleic acids including, but not limited to, polymerase chain reaction (PCR), self-sustained sequence replication, strand-displacement amplification, "branched chain" DNA amplification, ligase chain reaction (LCR) and Q-Beta replicase amplification (QBR). In some embodiments of the present invention, the selected nucleic acids are amplified using PCR.

The step of selecting a second subpopulation comprising at least one nucleic acid species from the first subpopulation, wherein the at least one nucleic acid species is internalized by said cell of interest includes, but is not limited to, such detection methods as fluorescence microscopy and flow cytometry, including, but not limited to, fluorescent-activated cell sorting.

To aid in detection, the at least one nucleic acid from the first subpopulation may be labeled with a detectable label using methods standard in the art, wherein the dectable label can include, but is not limited to, fluorescent dyes, fluorophores, chromophores, affinity labels, metal chelates, chemically reactive groups, enzymes, radionuclides, electrochemically detectable moieties, and energy absorbing or energy emitting compounds.

Fluorescent dyes that can be used with the present invention are any capable of binding to nucleic acids as defined herein and include, but are not limited to, the coumarin dyes, acetyl azide, fluorescein isothiocyanate, 1,2-dihexadecanoyl-sn-glycero-3-phosphoethanolamine, 8-(6-aminohexyl)aminoadenosine 3',5'-cyclicmonophosphate, bis(triethylammonium) salt, rhodamine dyes, sulfonyl chloride, CyDye™ fluors, and carboxynaphtofluorescein. The haptenes that may be used for labeling include, but are not limited to, biotin, digoxigenin, and 2,4-dinitrophenyl. The haptenes require fluorescently-labeled antibodies or specific proteins for visualization/detection.

Labeling of nucleic acids with electrophore mass labels is described, for example, in Xu et al., J. Chromatography 764: 95-102 (1997). Electrophores are compounds that can be detected with high sensitivity by electron capture mass spectrometry (EC-MS). Electrophore mass labels can be attached to a probe using chemistry that is well known in the art for reversibly modifying a nucleotide (e.g., well-known nucleotide synthesis chemistry teaches a variety of methods for attaching molecules to nucleotides as protecting groups). Electrophore mass labels are detected using a variety of well-known electron capture mass spectrometry devices. Further, techniques that may be used in the detection of electrophore mass labels include, for example, fast atomic bombardment mass spectrometry (See Koster et al., Biomedical Environ. Mass Spec. 14:111-116 (1987)); plasma desorption mass spectrometry; electrospray/ionspray (See Fenn et al., J. Phys. Chem. 88:4451-59 (1984), PCT Appln. No. WO 90/14148, Smith et al., Anal. Chem. 62:882-89 (1990)); and matrix-assisted laser desorption/ionization (Hillenkamp et al. *Biological Mass Spectrometry* (Burlingame and McCloskey, eds.), Elsevier Science Pub., Amsterdam, pp. 49-60, 1990); Huth-Fehre et al., *Rapid Communications in Mass Spectrometry,* 6:209-13 (1992)). (See also U.S. Pat. No. 6,979,548 issued to Ford et al.)

Methods for conjugation of detectable labels to nucleic acids are well known in the art, for example, Schubert et al., *Nucleic Acids Research* 18:3427 (1990) Smith et al., *Nature,* 321:674-679 (1986); Agarawal et al., *Nucleic Acids Research,* 14:6227-6245 (1986); Chu et al., *Nucleic Acids Research,* 16:3671-3691 (1988).

Sequencing at least one selected nucleic acid from a second subpopulation may be done according to methods standard in the art including, but not limited to, automated nucleic acid sequencing procedures as disclosed in Naeve, C. W., (1995) *Biotechniques* 19:448, and sequencing by mass spectrometry. See, e.g., PCT International Publication No. WO 94/16101; Cohen et al., *Adv. Chromatogr.* 36:127-162 (1996); and Griffin et al., *Appl. Biochem. Biotechnol.* 38:147-159 (1993).

Incorporation of a compound of interest into a selected nucleic acid sequence requires that the selected nucleic acid sequence retains its original three-dimensional structure of the native sequence following the incorporation. In some embodiments, folding calculations are performed to compare the predicted folding patterns of the chemical structure of the native nucleic acid sequence with that of a nucleic acid sequence incorporating one or more compound of interest. Calculations can be performed with, e.g., folding programs such as mFOLD (Michael Zuker, Burnet Institute). Such calculations apply an algorithm to the native sequence of the nucleic acid to determine folding patterns that yield the most stable secondary structures. This approach provides insight into the likely location of double helical regions that occur within the three-dimensional structure of the nucleic acid. The structural characteristics of the native and modified nucleic acids can also be determined using circular dichroism (CD) spectroscopy and ultraviolet (UV) hyperchromicity measurements. Other methods of comparison will be apparent to those skilled in the art. Preferred nucleic acids of interest are those that incorporate compounds of interest in such a way as to not significantly alter the folding characteristics of the native sequences.

In some embodiments, modified nucleic acids are further evaluated for the extent to which they selectively kill cells of interest, e.g., through the release of cytotoxic nucleotides by 3'-O-exonucleolytic degradation. Cell viability can be evaluated, e.g., using 3-(4,5-dimethythiazole-2-yl)-5-(3-carboxymethoxyphenyl)-2-(4-sulfophenyl)-2H-tetrazolium, inner salt (MTS) assays. Preferred nucleic acids are those that are cytotoxic towards cells of interest and not cytotoxic to non-targeted cells.

Synthesizing a nucleic acid having a sequence corresponding to a selected nucleic acid and incorporating a compound of interest may done according to any method standard in the art including, but not limited to, de novo chemical synthesis of polynucleotides, such as by presently available automated DNA synthesizers, and standard phosphoramidite chemistry. De novo chemical synthesis of a polynucleotide can be conducted using any suitable method, including, but not limited to, the phosphotriester or phosphodiester methods. See Narang et al., *Meth. Enzymol.,* 68:90 (1979); U.S. Pat. No. 4,356,270; Itakura et al., *Ann. Rev. Biochem.,* 53:323-56 (1989); Brown et al., *Meth. Enzymol.,* 68:109 (1979); and U.S. Pat. No. 6,911,310 issued to Heller. In one embodiment of the present invention, automated nucleic acid synthesis is conducted using an Applied Biosystem 394™ automated DNA/RNA synthesizer (Applied Biosystems, Foster City, Calif.).

In some embodiments of the present invention, a synthetic nucleic acid may comprise one compound of interest. In other embodiments, a synthetic nucleic acid may incorporate more than one compound of interest. In some embodiments, one of the compounds of interest incorporated into the synthetic nucleic acid may be a detectable compound, and/or an active compound.

In preferred embodiments, cytotoxic oligodeoxynucleotides are oligodeoxynucleotides (ODNs) that contain one or more cytotoxic nucleoside analogs. Once incorporated into an ODN, the 5'-O-monophosphate form of the nucleoside is present as an intact unit that is embedded in the ODN polymer. The cytotoxic nucleoside analogs may be incorporated as a stretch of several ODNs, or may be incorporated at various places in the nucleotide species. In some embodiments, cytotoxic ODNs are arranged as a stretch of 2, 3, 4, or 5 to 20, 25, 30, or 40 ODNs. A preferred example of a cytotoxic ODN is FdUMP[10], a linear homopolymer of FdUMP, the thymidylate synthase inhibitory metabolite of the anticancer drug 5-fluorouracil (5FU). (Gmeiner, Curr. Med. Chem. 12: 1345-1359 (2005); Gmeiner et al., Nucl. Nuct. Nucl. Acids 23: 401-410 (2004)). Another preferred example is FdUMP[5], illustrated in FIG. 1. The cytotoxic ODNs may be included in the synthesis of a desired nucleotide species, or may be appended to a desired nucleotide species. Synthesis and toxicity of FdUMP are found in U.S. Pat. No. 5,457,187 (Gmeiner et al.); U.S. Pat. No. 5,614,505 (Gmeiner et al.); U.S. Pat. No. 5,663,321 (Gmeiner et al.); U.S. Pat. No. 5,741,900 (Gmeiner et al.); and U.S. Pat. No. 6,342,485 (Gmeiner).

In some embodiments, ODNs may be synthesized to incorporate compounds of interest such as cytotoxic nucleoside analogs, either before or after the enrichment selections of candidate ODN sequences. In a preferred embodiment, ODNs selected in the first and second pools do not comprise a compound of interest. The selected ODNs are sequenced and analyzed to determine whether the incorporation of a compound on interest will affect their activity towards a biological target of interest. Cytotoxic ODNs are then subsequently synthesized consistent with analysis predictions (e.g. predicted folding). However, synthesis of ODNs containing a compound on interest such as a cytotoxic nucleoside analog may also be performed prior to the enrichment steps.

Modified ODNs of the present invention can be optimized, e.g., for treatment of PC and other malignancies. In some embodiments of the present invention, the modified ODNs target xPSM using FdUMP as the active drug. In other embodiments, the modified ODNs target extracellular surface proteins that are differentially expressed specifically on the surface of certain PC cells (e.g. prostate stem cell antigen). In further embodiments the modified ODNs administered to a particular patient may be customized to reflect the protein profile expressed by a specific patient. Additionally, the choice of drugs for inclusion into the modified ODN structure may be expanded to reflect the drug-profile that provides the maximum response for a particular malignancy. The ODNs of the present invention are compatible with a wide-range of cytotoxic compounds, including, but not limited to, nucleoside analogs, cytotoxic drugs, radionuclides, modifiers of gene expression and nanoparticles.

EXAMPLE 1

Identification of Oligodeoxynucleotide Sequences that Undergo Facilitated Uptake into Prostate Cancer Cells as a Consequence of Binding to the Extracellular Domain of Prostate Specific Membrane Antigen In order to identify oligodeoxynucleotide (ODN) sequences that bind to the extracellular domain of prostate specific membrane antigen (xPSM) and undergo facilitated uptake into PC cells as a consequence of xPSM binding, a pool of random ODN sequences that is sufficiently large and complex was used. Within this pool, the ODN sequences fold into a three-dimensional structure. Certain species within this pool bind xPSM with high affinity. Rounds of selective binding of ODNs to an xPSM-affinity matrix are used to identify sequences of interest. ODN sequences that bind xPSM with high affinity are amplified using PCR. ODN sequences that undergo selective facilitated uptake into PC cells, such as those of LNCaP cell line, are candidate cytotoxic ODNs (i.e., the ODN sequences that contain cytotoxic nucleotides and that selectively enter and kill PC cells).

A. Preparation of xPSM Affinity Matrix.

A protocol was designed to express the 706 amino acids comprising the extracellular domain of PSMA from Sf-9 (insect) cells using baculovirus. Pelleted LNCaP cells (quick frozen in liquid $N_2$) were used as the source of RNA for cloning of PSMA. RNA was extracted from the pelleted cells and the integrity of the RNA was verified by gel electrophoresis. First strand cDNA synthesis was accomplished by reverse transcription using oligo dT(N) and random hexamer primers, and SENSISCRIPT™ reverse transcriptase (Qiagen). The cDNA was purified using a Qiagen column. Primers were designed by standard procedures for cloning of the extracellular domain of PSMA into the pBacGus3 plasmid (Novagen). The 5'-primer includes an XbaI site to facilitate cloning into the NheI site in the vector (pBacGus3). The 3'-primer includes a HindIII site for cloning into the HindIII site of pBacGus3. The 3'-primer was also designed to express a His-tag sequence in the vector to attach the protein to magnetic beads for use as an affinity matrix. The target region of the PSMA gene was amplified from cDNA by PCR using PHUSION™ high-fidelity DNA polymerase (New England Biolabs) to yield a product of the expected length (~2.2 kB). The PCR product was successfully cloned into the pBacGus3 shuttle vector with 6 out of 6 colonies showing the insert.

Procedures for the expression of human xPSM from Sf-9 cells using baculovirus are known in the art. The His-tagged xPSM protein was bound to M450 magnetic beads (Dynal Biotech). The suitability of the xPSM beads for ODN selection was verified by determining that a known RNA aptamer sequence to xPSM binds to the beads (Lupold et al., Cancer Res. 62: 4029-4033 (2002)). The xPSM-beads were then used for the identification of ODNs that bind xPSM with high affinity, using the procedures described in the following section.

B. Selection of ODNs that Bind xPSM with High Affinity.

The exponential enrichment methodology used to identify ODNs with high binding affinity for xPSM has been described previously (Morris et al., Proc. Natl. Acad. Sci. USA 95: 2902-2907 (1998); FIG. 2). A single-stranded DNA library was prepared on a 2 micromol scale containing a 45 nucleotide (45 mer) random sequence flanked by two 21 nucleotide constant regions. One of the two constant regions that flank the random 45 mer region of the DNA library construct consists of predominantly A-nucleotides and results in the ODN sequences selected for xPSM binding affinity having dT-residues predominantly in the 3'-terminus. Thus, the first constant region is a 21 mer fixed sequence, the random region is a 45 mer variable sequence, and the second constant region is a 21 mer fixed sequence that is adenine-rich (see FIG. 2). T-rich primers used for PCR amplification that are complementary to the A-rich constant region are biotinylated at the 5' terminus. The amplified DNA is purified on streptavidin beads to obtain single-stranded ODNs.

The single-stranded DNA library was gel-purified to yield 6.9 nmol of material ($4.16\times10^{15}$ molecules). The single-stranded material was next converted to dsDNA using a series of "fill-in" reactions with T7 DNA polymerase. These "fill-in" reactions were each run using 2 μg of the ssDNA library, a 1.5-fold excess of the 21 nucleotide primer complementary to the 3'-region of the ssDNA, 1.5 μL of 10 mM dNTPs, 5 units of T7 DNA polymerase (Fermentas), and 5 μL of 10× reaction buffer (400 mM Tris-HCl, 100 mM $MgCl_2$, 10 mM DTT), in a 50 μL total reaction volume. Reactions were incubated for 2 minutes at 37° C. and stopped by heating the reaction to 70° C. for 10 minutes. dsDNA was recovered by ethanol precipitation, analyzed by agarose gel electrophoresis, and quantified by UV absorption at 260 nm. Gel electrophoresis confirmed that essentially all of the ssDNA was converted to dsDNA using the T7 DNA polymerase "fill-in" reaction.

The dsDNA (0.35 nmol ($2\times10^{14}$)) was amplified for 5 cycles by PCR. Each PCR reaction includes 42.6 ng of template DNA and ~50-fold excess of the primers complementary to the 3'-terminus of each strand. The primer for the DNA strand produced in the T7 DNA polymerase "fill-in" reaction is biotinylated so that amplification of the original ssDNA containing the 30 mer random sequence will yield biotinylated DNA that can be separated using Streptavidin agarose.

For forward rounds of selection, 5-10 μg of annealed ssDNA in 100 μL of 100 mM NaCl, 20 mM Tris, 2 mM $MgCl_2$, 5 mM KCl, 1 mM $CaCl_2$ with 0.02% Tween-20 were incubated together with the affinity matrix for 60 min at 37° C. The supernatant was then removed. Bound material is eluted by heating to 95° C. in the presence of 20 μL of 5 μM 5'-phosphorylated primer followed by removal of the supernatant. The ssDNA that bound tightly to the magnetic beads was then converted to dsDNA using the T7 fill-in procedure and then ethanol precipitated. The material is then amplified by PCR and converted to ssDNA using exonuclease□ λ. For counter-selection, 5-10 μg of annealed ssDNA were incubated with magnetic beads without PSMA.

The sequences of ssDNA that resulted from multiple rounds of selection are determined by converting the material to dsDNA using a T7 fill-in reaction and then cloning the dsDNA into the pGEM T-Easy vector (Promega). dsDNA for the cloning procedure was gel-purified on a 2% agarose gel and purified using the SV wizard gel clean-up kit (Promega). The pGEM plasmid was then transformed into competent BL21 *E. coli* cells and screened for β-galactosidase activity. Sequences are determined according to standard methods of sequencing nucleic acids.

C. Selective Uptake of ODNs Into PC Cells.

ODNs selected for high binding affinity to xPSM are further evaluated for selective binding to PC cells that express xPSM. Fluorescence microscopy is used to investigate the selective binding of ODNs to PC cells that express xPSM, such as LNCaP, relative to those that do not express xPSM (e.g., PC-3 cells). The ODN sequences are chemically synthesized and 5'-conjugated with a fluorescent dye, such as rhodamine, using methods similar to those previously described (Lupold et al., Cancer Res. 62: 4029-4033 (2002)).

The binding and uptake of fluorescent-conjugated ODNs into PC cells is determined using a Zeiss confocal microscope. In addition, cellular uptake is quantified using $^{32}$P-labeled ODNs. The time-dependent accumulation of $^{32}$P-labeled ODN in PC cellular lysates is detected using a scintillation counter.

EXAMPLE 2

Analysis, Evaluation and Testing of the Selective Cytotoxicity of Modified ODNs Towards PC Cells A. Analysis of Modified ODN Sequences.

ODN sequences that are identified based upon selective facilitated uptake into LNCaP cells are synthesized with cytotoxic nucleotides (5-fluoro-2'-deoxyuridine (FdU)) in place of native nucleotides (Gmeiner et al., Nucl. Nuct. Nucl. Acids 23: 401-410 (2004)). Because introducing non-native nucleotides into the ODN sequence may alter the affinity for xPSM, the affinity of the substituted ODN relative to the native sequence is evaluated using gel-shift assays (Ferber et al., Anal. Biochem. 244: 312-320 (1997)). If introduction of FdU at certain sites substantially reduces affinity of the ODN for xPSM, NMR and/or X-ray studies are performed to identify sites for substitution that are less likely to affect binding affinity.

B. Synthesis of Candidate Modified ODNs.

The chemical synthesis of modified aptamers is performed using an automated DNA synthesizer at a commercial DNA synthesis facility. The FdU-phosphoramidite is synthesized using methods previously described (Gmeiner et al., Nucl. Nuct. Nucl. Acids 23: 401-410 (2004)).

The RNA aptamer A10-3 was synthesized. A10-3 is a 56 mer RNA sequence that binds the extracellular domain of PSMA (xPSM) with high affinity. The sequence for A10-3 (herein "parent aptamer") is 5'rGGGAGGACGAUGCG-GAUCAGCCAUGUUUACGUCAC UCCUUGUCAAUC-CUCAUCGGC-3' (SEQ ID NO:1). The 3'-terminus of A10-3 was modified with FdUMP to engineer cytotoxicity into the aptamer. Specifically, a modified aptamer containing the parent A10-3 sequence with 9 FdU nucleotides and one dC nucleotide appended to the 3'-terminus (A10-3: FdU[9]dC) was prepared. The dC nucleotide was required for synthesis of this RNA-DNA hybrid modified aptamer. The negative control was a modified aptamer with dT in place of FdUMP (A10-3: dT[10]).

For studies evaluating the specific uptake of the modified aptamers into targeted (LNCaP) versus non-targeted PC cells (PC3), modified aptamers with fluorescent dyes (either FAM or HEX) at the 5'-terminus were prepared. These modified aptamers included a reverse (3'→5') linkage at the 3'-terminus to reduce exonucleolytic degradation (5'-FAM-A10-3 and 5'-FAM-A10-3: dT[10]).

Modified aptamers that have been prepared include:

(a) A10-3:FdU[9]dC. This modified aptamer with 9 FdU nucleotides and one dC nucleotide appended to the 3'-terminus was synthesized to evaluate selective cytotoxicity towards targeted cancer cells.

(b) A10-3-$T_4$. This modified aptamer with four T deoxynucleotides replacing four U ribonucleotides in the aptamer sequence was synthesized to determine if deoxynucleotide substitution would change the three dimensional structure of the aptamer.

(c) A10-3-$FdU_4$. This modified aptamer with four FdU deoxyribonucleotides replacing four U ribonucleotides in the aptamer sequence was synthesized to determine if FdU substitution at internal positions of the aptamer sequence would result in selective cytotoxicity towards targeted cancer cells.

(d) A10-3-$FdU_4$:FdU[9]dC. This modified aptamer includes a total of 13 FdU deoxyribonucleotides (four at internal positions and nine appended at the 3'-terminus). This is used to evaluate selective cytotoxicity towards targeted cancer cells.

(e) A "scrambled" version of the A10-3 RNA aptamer sequence (SCR). This sequence has the same nucleotide composition and length as A10-3, but has the nucleotides in a different order. The SCR sequence is:

```
                                        (SEQ ID NO: 2)
5' rCAGGCAUGCCUAGCUAAGCAGCCCAUGGCUUAUGCGCGGAAUAUUG

GCUUCCGUUC
```

(f) 5'-FAM-SCR:T[10]. This modification of the scrambled aptamer sequence included a fluorescent dye and 10 T deoxynucleotides appended at the 3'-terminus. The scrambled aptamer sequence was used as a negative control to verify that the native aptamer structure was required for selective uptake into targeted cancer cells.

(f) SCR:FdU[9]dC. This modified scrambled aptamer sequence was used to determine the extent that the native aptamer structure was required for selective cytotoxicity towards targeted cancer cells.

C. Folding Analysis of Candidate Modified Aptamers.

Engineering cytotoxicity into an existing aptamer sequence, such as A10-3, requires that the aptamer retain the original three-dimensional structure following the substitution of cytotoxic drugs into the native sequence. To gain insight into the structure of A10-3, mFOLD calculations were performed. The mFOLD calculations apply an algorithm to the primary sequence of the RNA to determine folding patterns that yield the most stable secondary structures. This approach provides insight into the likely location of double helical regions that occur within the three-dimensional structure of the A10-3 aptamer.

Figure 3:
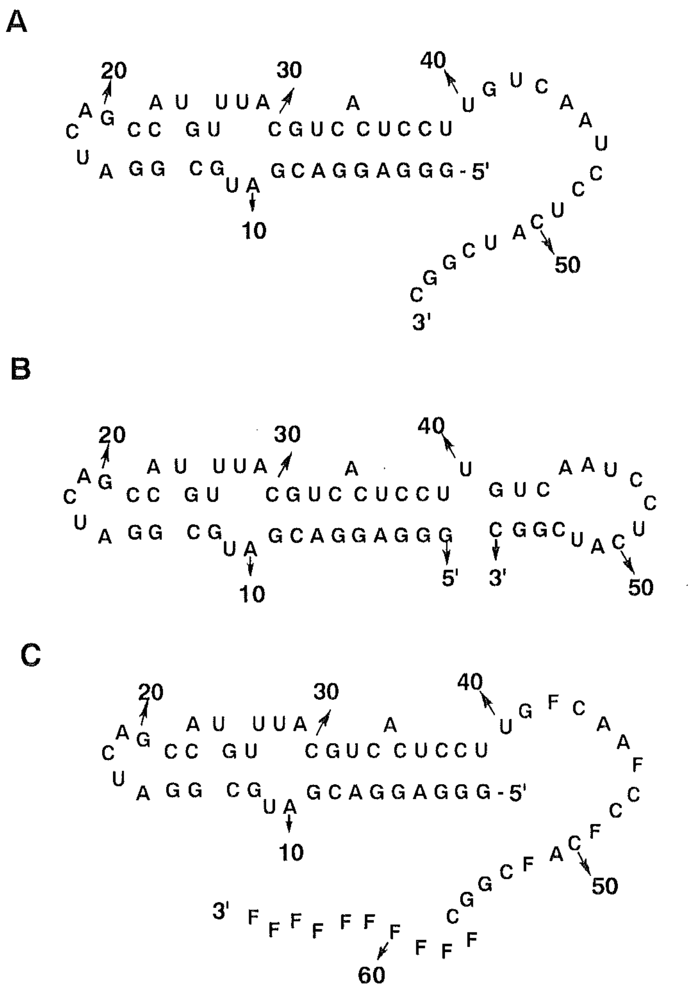
FIG. 3. The lowest energy (A) and second lowest energy (B) secondary structures of the A10-3 aptamer (SEQ ID NO:1) as predicted from the primary sequence using mFOLD. (C) Proposed secondary structure for a modified aptamer generated from the A10-3 aptamer sequence (SEQ ID NO:3).

The two lowest energy folds identified by the mFOLD program for the A10-3 aptamer are shown in FIGS. 3(A and B). Both of the lowest energy secondary structures contain a helical region consisting of nine base pairs with a single bulged A. Both of the lowest energy structures also contain a short stem loop consisting of four base pairs and a five-base loop. The major difference between the two lowest energy structures is for the 16 nucleotides at the 3'-terminus of the sequence. The lowest energy structure predicts no base pairing between nucleotides in this region, while the second lowest energy structure predicts base pairing between nucleotides 41-43 and the three nucleotides at the 5'-terminus. Based on this analysis of secondary structure motifs for the A10-3 sequence, appending deoxynucleotides to the 3'-terminus of A10-3 was predicted to have an insignificant effect on the double helices important for the three-dimensional structure formation of A10-3. It also appeared likely that substitution of U ribonucleotides near the 3'-terminus with FdU deoxynucleotides would have minimal effect on the A10-3 structure (FIG. 3C). Subsequent circular dichroism (CD) studies of T- and FdU-substituted aptamers revealed that insertion of these deoxyribonucleotides had minimal effect on aptamer structure or stability.

D. Circular Dichroism and Ultraviolet Analysis of Candidate Modified Aptamers.

Figure 4:
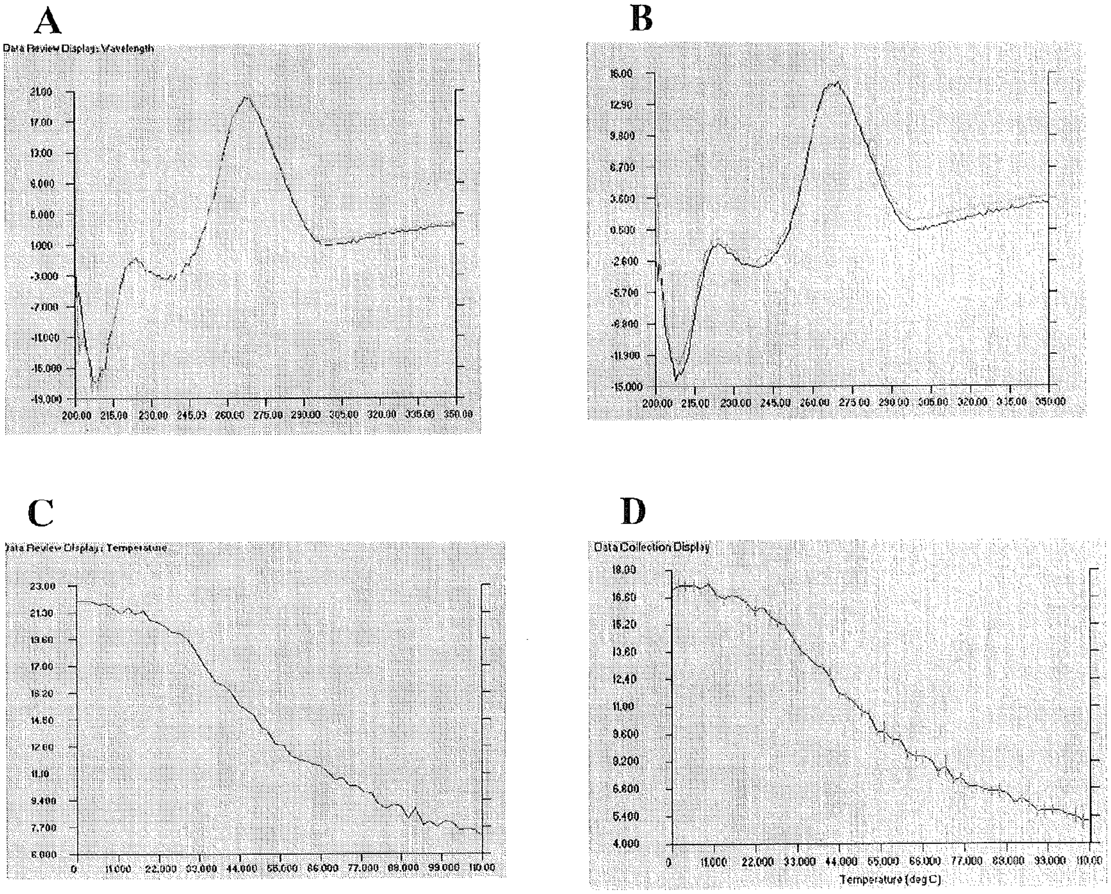
FIG. 4. Circular dichroism spectra and UV thermal melt data of the modified A10-3 aptamer (A) and (C), respectively, and the parent A10-3 aptamer (B) and (D), respectively.

The structural characteristics of the parent aptamer and modified aptamers were determined using circular dichroism (CD) spectroscopy and ultraviolet (UV) hyperchromicity measurements. The data for the CD spectroscopy are shown in FIGS. 4A (modified aptamer) and 4B (parent aptamer). The circular dichroism curve acquired before thermal melting is in blue and that obtained post-melt is green. A maximum positive ellipticity is observed at 270 nm consistent with a highly folded structure, probably consisting of A-form helices. The circular dichroism spectra for the modified aptamers are indistinguishable from circular dichroism spectra for the parent aptamer. The UV thermal melt data is shown in FIGS. 4C (modified aptamer) and 4D (parent aptamer). The melting temperature for parent aptamer and the modified aptamers is about 55° C. Both the parent aptamer and the modified aptamers adopt highly folded structures that are stable at 37° C. These data indicate that the modification of the aptamer sequence had minimal effect on structure and thus was not likely to effect binding to the PSMA target or cellular uptake in cells that express PSMA.

E. Internalization of Modified Aptamers By Targeted Cancer Cells.

The specific uptake of modified aptamers into targeted cancer cells was observed using fluorescence microscopy. The human prostate cancer cell line LNCaP was used as the cellular target for the modified aptamers because it is known to express xPSM. PC3 (human prostate cancer) cells were used as the negative control as they are known not to express xPSM. Cells were grown to the desired level of confluency (~50%) in 35 mm dishes. The fluorescently labeled modified aptamer (with and without the dT[10] tail) was then added to the medium at 1 micromolar concentration, and the cells were incubated for various time intervals (e.g. 15 min, 30 min, 45 min, etc.). The medium containing the dye was then removed, and the cells were washed with culture medium. Following the washes, the cells were placed in PBS and viewed under a Zeiss Axiovert confocal microscope in the core microscopy laboratory of the Comprehensive Cancer Center at Wake Forest University. The results are shown in FIG. 5.

Figure 5:
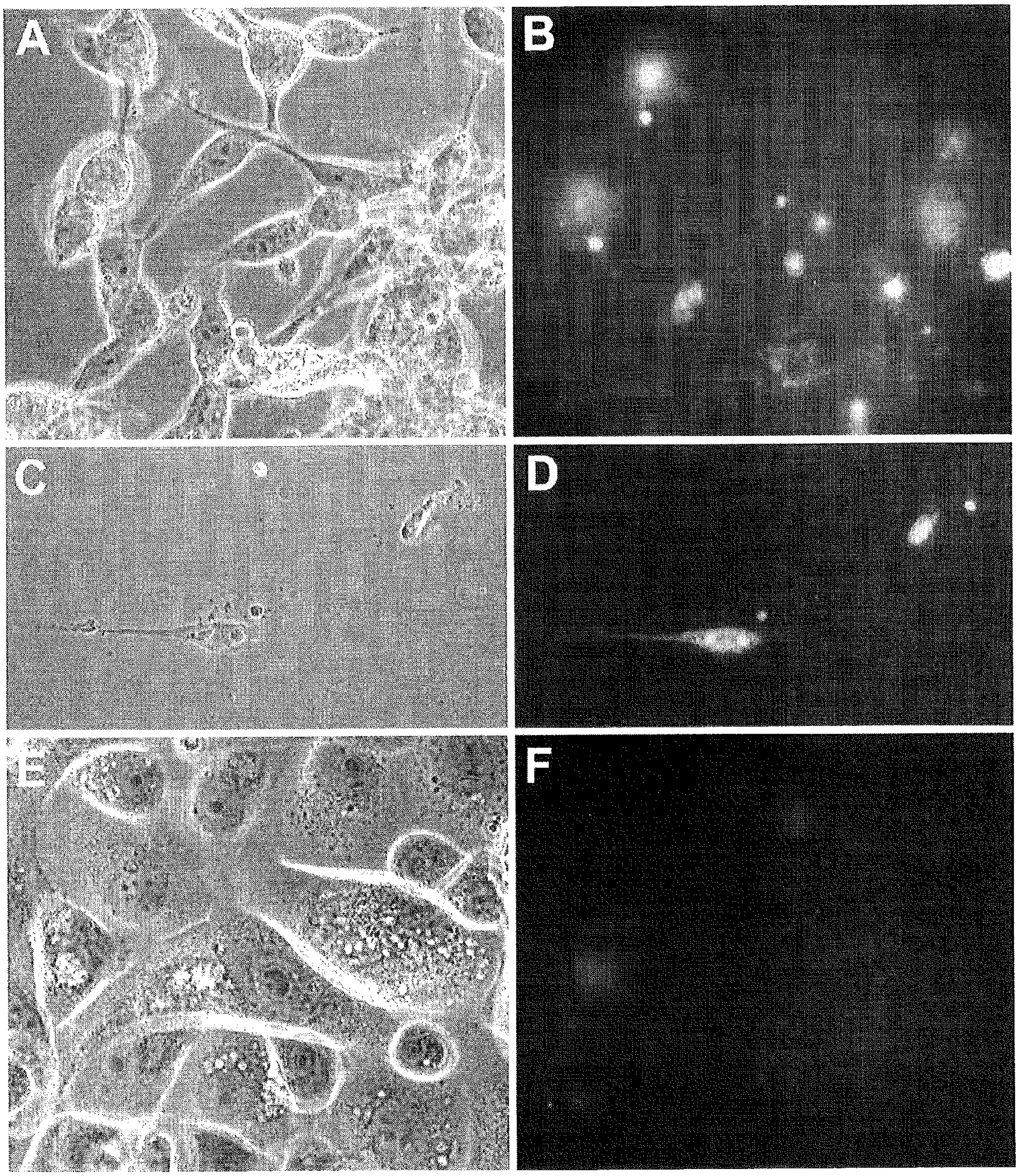
FIG. 5. Fluorescence and phase contrast images of LNCaP and PC3 cells following exposure to modified A10-3 aptamers conjugated with the FAM dye. The fluorescence images of LNCaP cells following a 15 min or 45 min exposure to the modified aptamer are shown in FIGS. 5B and 5D, respectively. The corresponding phase contrast images are shown in FIGS. 5A and 5C.

FIG. 5 shows fluorescence images of LNCaP cells following 15 min (B) or 45 min (D) exposure to the modified aptamer. The fluorescent aptamer was localized predominantly in the nucleus. The corresponding phase contrast images are shown in FIGS. 5A and 5C, respectively. FIGS. 5E and 5F, respectively, show the phase contrast and fluorescence microscopy images of PC3 cells following 30 min exposure to the modified aptamer. Little uptake of the aptamer is observed in healthy PC3 cells. All cells were exposed to approximately 1 micromolar concentration of the fluorescent modified aptamer for the indicated times. Uptake of 5'-FAM-A10-3:T[10] occurred rapidly into nearly all LNCaP cells. Substantial uptake was observed with as little as 15 minutes of exposure into these cells. 5'-FAM-A10-3:T[10] localized mainly in the nuclei of LNCaP cells. In contrast, uptake of 5'-FAM-A10-3:T[10] was limited to only a small percentage of PC3 cells and these cells appeared to be among the least robust upon inspection by phase contrast microscopy. No specific sub-cellular localization of 5'-FAM-A10-3:T[10] was observed in PC3 cells. These results demonstrate that modified aptamers, such as 5'-FAM-A10-3:T[10], are rapidly and selectively taken up by PC cells that express PSMA on the extracellular surface of the plasma membrane.

F. Cytotoxicity of Candidate Modified Aptamers.

The candidate modified ODNs are evaluated for the extent to which they selectively kill PC cells through the release of cytotoxic nucleotides by 3'-O-exonucleolytic degradation. The ODN sequences are synthesized using standard automated methods with phosphoramidites derived from cytotoxic nucleosides used in place of the native nucleotides. For example, at any location in a particular ODN sequence where a dT is located, FdU is inserted. Cytotoxic analogs of dA, dC, and dG may also be inserted in place of these native nucleotides. The cytotoxicity of these candidate modified ODNs is evaluated with regard to PC cells that express xPSM (e.g. LNCaP), to PC cells that do not express xPSM (e.g. PC3), and to normal prostatic epithelial cells. Uptake kinetics for modified ODNs are calculated from the time- and concentration-dependence of $^{32}P$-labeled modified aptamers in target cells. The mechanisms for the cytotoxicity of the modified ODNs that are investigated include thymidylate synthase inhibition, nucleotide pool imbalance, and DNA damage using methods previously described (Gmeiner et al., Nucl. Nuct. Nucl. Acids 23: 401-410 (2004)).

The cytotoxicity of candidate modified aptamers towards LNCaP and PC3 cells is evaluated using 3-(4,5-dimethythiazole-2-yl)-5-(3-carboxymethoxyphenyl)-2-(4-sulfophenyl)-2H-tetrazolium, inner salt (MTS) assays. Cells are grown in RPMI 1640 medium (Life Technologies, Rockville, Md.) supplemented with 10% FBS, 5 mM glutamate, penicillin (100 U/mL) and streptomycin (100 μg/mL) at 37° C. in a 5% $CO_2$ atmosphere. The cytotoxicity of the candidate modified aptamers is evaluated over the concentration range $10^{-12}$-$10^{-6}$ M with 48 h drug exposure. Cell viability is assessed using the MTS assay according to the manufacturer's protocol. Absorbance values for the formazon dye are measured using an automated plate reader (Molecular Dynamics, Sunnyvale, Calif.). $IC_{50}$ values are calculated from the data using GRAPHPAD™ software (GraphPad Software, Inc., San Diego, Calif.). Each experiment is performed in triplicate.

The cytotoxicity of the candidate modified aptamers is also evaluated with regard to prostate cells that have been obtained from normal prostate tissue derived from radical prostatectomies. A procedure for establishing primary human epithelial cell cultures from the disease-free regions of the tissue (based on histology) has been described (Peehl et al., In Vitro Cell Dev. Biol. 22: 90 (1986); Peehl et al., In Vitro Cell Dev. Biol. 24: 530-536 (1988); Barreto et al., Cancer Epidemiol. Biomarkers Prev. 9: 265-270 (2000). The cultures are grown in MCDB 105 medium (Sigma, St. Louis, Mo.) that has been supplemented with growth factors and hormones as described previously (Peehl et al., In Vitro Cell Dev Biol 22: 90 (1986)). Trypan blue exclusion is used as a marker of viable cells. The data are analyzed to identify those candidate modified aptamers sequences that are highly efficient at killing PC cells that express xPSM, but that are not cytotoxic towards normal prostate cells. Candidate modified aptamers that display the greatest differential cytotoxicity are further developed as drugs for the treatment of human PC.

Results from a NCI 60 cell line screen show that FdUMP [10] is cytotoxic towards prostate cancer cells at physiologically relevant drug concentrations (10 nM-100 nM). Further, FdUMP [10] was found to be substantially more cytotoxic towards prostate cancer cells than either 5FU or FdU which are potential degradatory products of FdUMP[10]. MTS assays and clonogenic assays also show that FdUMP[10] is substantially more cytotoxic towards DU145 and PC3 prostate cancer cells than any monomeric fluoropyrimidine (5FU, FdU, FdUMP). These data are consistent with FdUMP[10] being able to penetrate prostate cancer cells in intact form, without prior degradation to monomeric fluoropyrimidine products.

Figure 6:
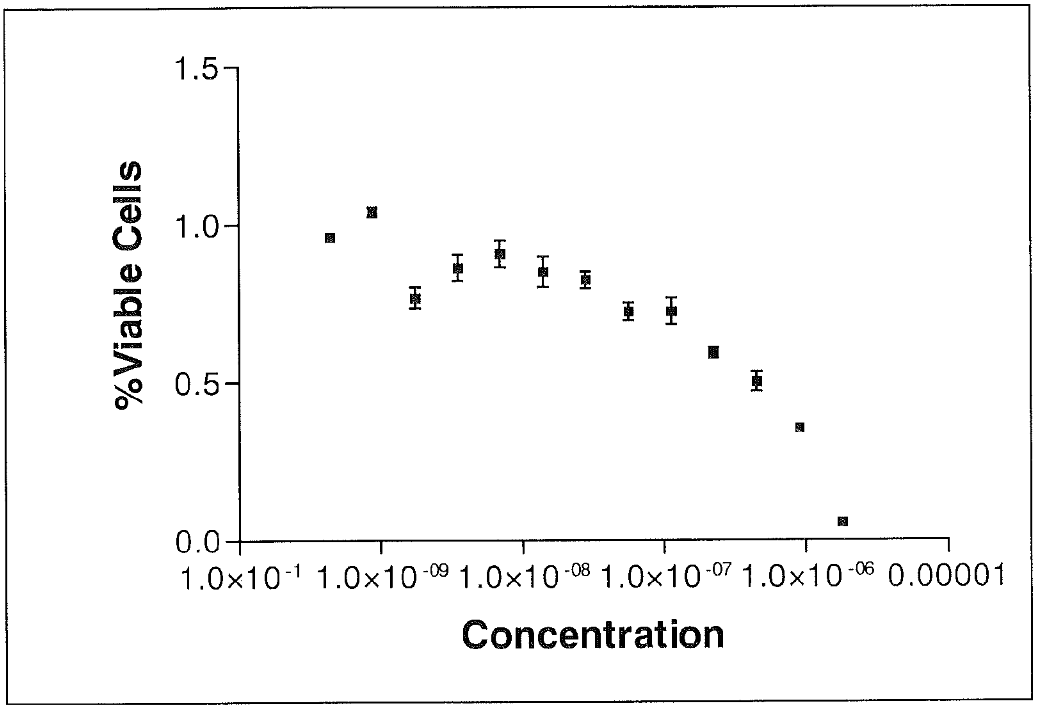
FIG. 6. The RNA aptamer modified to contain an FdUMP [9] tail shows dose-dependent cytotoxicity toward LNCaP prostate cancer cells.

The cytotoxicity toward LNCaP prostate cancer cells by a modified RNA aptamer containing a FdUMP[9] tail is illustrated in FIG. 6. As shown in FIG. 6, the RNA aptamer modified to contain an FdUMP [9] tail shows dose-dependent cytotoxicity toward the target prostate cancer cells.

Figure 7:
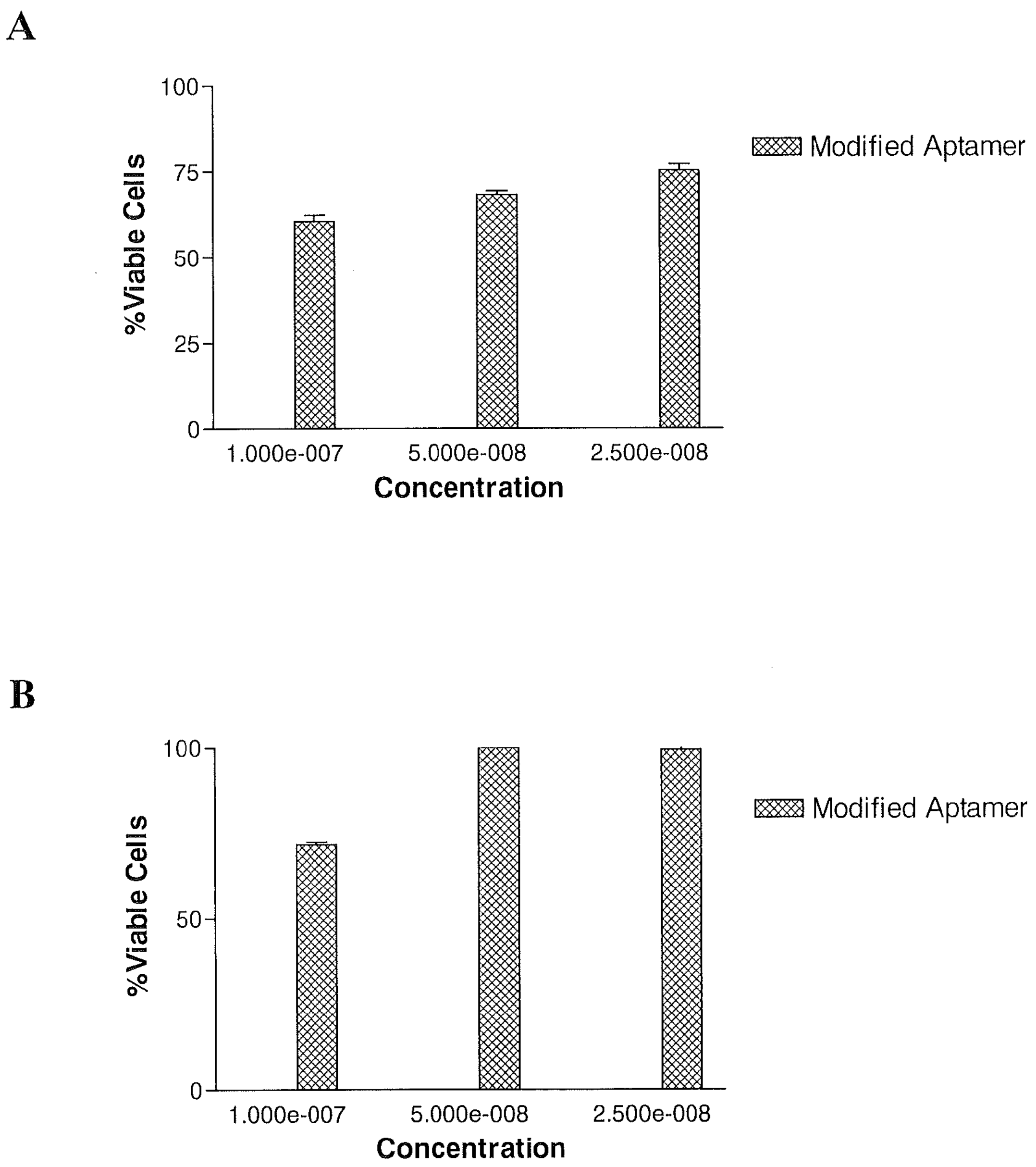
FIG. 7. Graphs of the percent viable cells following a 40 minute exposure to the modified aptamer and 48 hour incubation in drug free medium. (A) LNCaP cells; (B) PC3 cells.

FIGS. 7A and 7B further illustrate the cytotoxicity of the modified aptamers as assessed using the MTS assays. Since fluorescence microscopy studies indicated that substantial uptake of the modified aptamer occurred within 45 min in targeted LNCaP cells, the LNCaP cells (A) and the PC3 cells (B) were exposed to the modified aptamer for 40 min. Following exposure to the modified aptamer, the medium containing the modified aptamer was removed and replaced with fresh medium. The cells were then incubated for 48 hours, The 48 hours in drug-free medium allows cells to metabolize the modified aptamer and progress through the cell-cycle. Cell viability was measured using the MTS assay. Results show that the LNCaP cells express the PSMA target for the aptamer and display dose-dependent reduction in percent viable cells (FIG. 7A), The PC3 cells are less sensitive to the modified aptamer with no cytotoxicity at the lower concentrations (FIG. 7B).

To determine if extracellular degradation is important for the cytotoxicity of FdUMP[10] towards prostate cancer cells, cells were incubated with either an inhibitor of phosphatase activity or an inhibitor of nucleotidase activity. Neither inhibitor substantially reduced the cytotoxicity of FdUMP [10] towards PC cells, indicating that prostate cancer cells efficiently take up FdUMP[10] in multimeric form. Other types of cancer cells (e.g. colon cancer) were less efficient in uptake of FdUMP[10] multimer than were prostate cancer cells, These studies demonstrate that ODNs can be prepared which are selectively taken up by certain types of cancer cells. Studies have shown that ODNs can be taken up into cells by an endocytotic mechanism (Loke et al., Proc. Natl. Acad. Sci. USA 86: 3474-3478 (1989)).

Figure 8:
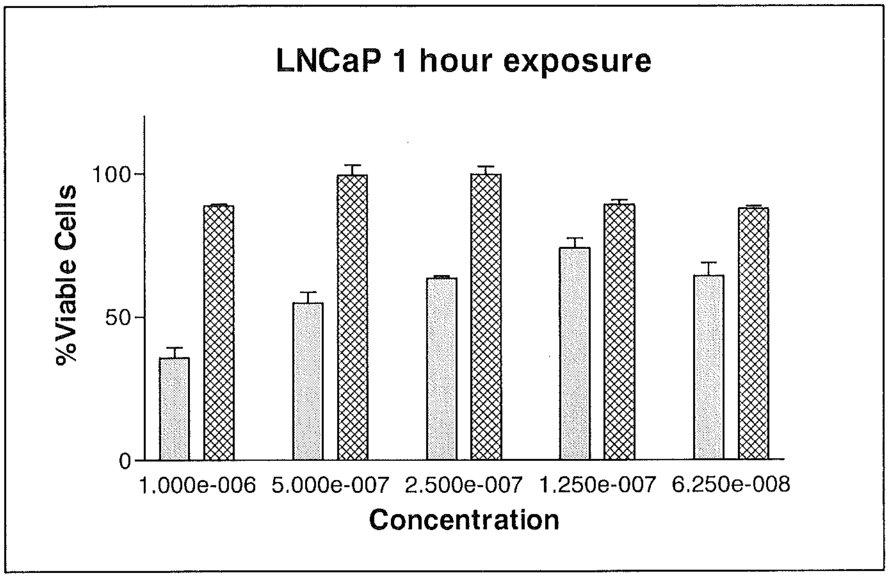
FIG. 8. Bar graphs indicating the percent viable cells following 1 hour treatment with A10-3:FdU[9]dC (solid bars) or A10-3:T[10] (hatched bars). LNCaP (A) and PC3 (B) cells were exposed to the modified aptamers for one hour.
Figure 8:
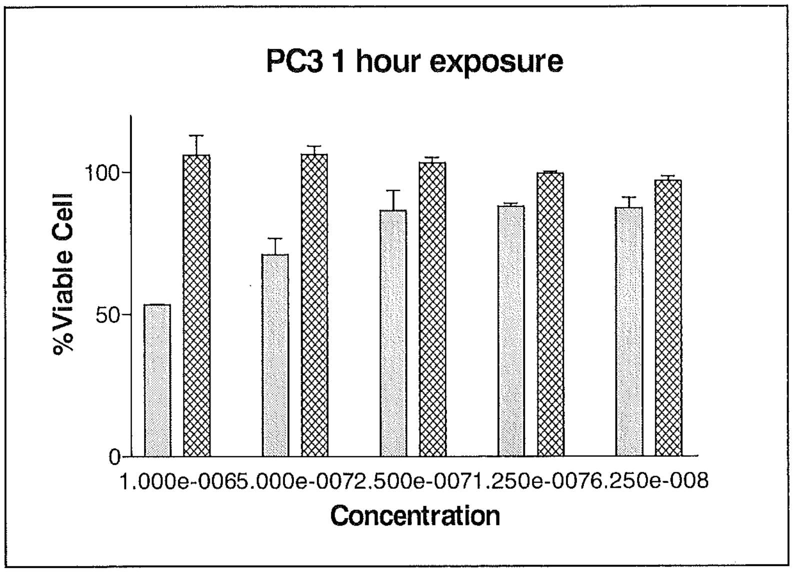

In addition, cytotoxicity has been assessed in LNCaP cells and PC3 cells using the MTS assay following a 1 hour exposure to several modified aptamers. After the one hour exposure the medium containing the drug was removed and replaced with fresh medium. The cells were then incubated for 48 h. Cell viability was measured using an MTS assay. The results from a typical experiment are shown in FIG. 8. The results show that the A10-3:T[10] aptamer does not reduce the viability of either LNCaP or PC3 cells over the concentration range evaluated ($1.0\times10^{-6}$–$6.25\times10^{-8}$ M). Thus, modified aptamers are not inherently cytotoxic to either LNCaP or PC3 cells. In contrast, the A10-3:FdU[9]dC aptamer decreased the viability of both LNCaP and PC3 cells in a concentration-dependent manner A10-3:FdU[9]dC decreased the viability of LNCaP cells to a greater extent than PC3 at all concentrations evaluated for a one hour drug exposure. The reduction in cell viability was nearly equal for longer exposure times. These data are consistent with the reduction in cell viability occurring from a combination of two processes: 1) Selective uptake of A10-3:FdU[9]dC into LNCaP cells via an endocytotic process; and 2) Extracellular degradation of A10-3:FdU[9]dC to release monomeric FdU. These results suggest that modifying the rate of extracellular degradation of modified aptamers may provide additional selectivity for targeted cancer cells.

The results also demonstrate the high degree of potency of A10-3:FdU[9]dC to PC cells. A one hour exposure to $1\times10^{-6}$ M A10-3:FdU[9]dC reduced the viability of PC3 cells by nearly 50% and reduced the viability of LNCaP cells to an even greater extent. Longer exposure times resulted in nearly complete loss of cell viability. These data are in sharp contrast to the effects of 5FU towards these cells. Studies from our laboratory and from the NCI 60 cell line screen have shown that FdUMP[10], a linear homopolymer of ten FdUMP nucleotides, is 1,585 time more potent than 5FU towards DU145 PC cells and 631 times more potent than 5FU towards PC3 cells. The $IC_{50}$ of FdUMP[10] towards DU145 cells is $5.01\times10^{-9}$ M ($GI_{50}$ value from the NCI 60 cell line screen) and both PC3 and LNCaP cells also are highly sensitive to FdUMP[10] (but not 5FU).

The mechanistic basis for the sensitivity of PC cells to FdUMP[10] (but not 5FU) is currently under investigation. PC cells may be highly sensitive to activated fluoropyrimidines (FPs; e.g. FdUMP and FdUTP) because FdU-substituted DNA acts as a topoisomerase 1 (Top1) poison. PC cells express relatively high levels of Top1 and are sensitive to other Top1 poisons, such as the camptothecins (CPTs). CPTs have not shown efficacy for treatment of PC as a result of dose-limiting toxicities. 5FU is not efficiently metabolized to FdUMP and FdUTP in PC cells and hence 5FU, and prodrugs of 5FU (e.g. capecitabine) are not useful for the treatment of PC. FdUMP[10] is very well-tolerated in vivo, and trypan blue exclusion assays show a large differential sensitivity between PC cells and normal prostatic epithelial cells. Modified aptamers are expected to have greater intrinsic stability in plasma relative to FdUMP[10] because they are highly structured. Thus, modified aptamers are expected to be even better tolerated in vivo than FdUMP[10], and also to display greater selective cytotoxicity for targeted PC cells than FdUMP[10].

The foregoing is illustrative of the present invention, and is not to be construed as limiting thereof. The invention is defined by the following claims, with equivalents of the claims to be included therein.

That which is claimed is:

1. A nucleic acid molecule, comprising:

(i) a nucleotide sequence that specifically binds to an extracellular surface protein expressed by a cell of interest, wherein the nucleotide sequence comprises SEQ ID NO:1; and (ii) a cytotoxic nucleotide, wherein the cytotoxic nucleotide comprises poly-FdUMP;

wherein the nucleic acid molecule ranges from about 30 nucleotides to about 150 nucleotides in length, wherein the poly-FdUMP comprises FdUMP[9] or FdUMP[10], wherein the poly-FdUMP is appended to the 3'-terminus of the nucleotide sequence, and wherein the poly-FdUMP further comprises a dC nucleotide appended to the 3'-terminus thereof.

2. The nucleic acid molecule of claim 1, wherein said extracellular surface protein is prostate specific membrane antigen (PSMA) and wherein the nucleic acid molecule is capable of being internalized by a cancer cell expressing said PSMA.

3. The nucleic acid molecule of claim 1, wherein the cell of interest is a cancer cell.

4. The nucleic acid molecule of claim 3, wherein the cancer cell is a prostate cancer cell.

5. The nucleic acid molecule of claim 4, wherein the extracellular surface protein is prostate specific membrane antigen (PSMA).

6. The nucleic acid molecule of claim 1, wherein the nucleic acid molecule is capable of being internalized by the cell of interest.

7. A nucleic acid molecule consisting of SEQ ID NO:1 and FdUMP[9]dC appended to the 3'-terminus of SEQ ID NO:1.

* * * * *